United States Patent
Barrall et al.

(10) Patent No.: US 7,635,364 B2
(45) Date of Patent: Dec. 22, 2009

(54) UNIDIRECTIONAL TRANSLATION SYSTEM FOR BONE FIXATION

(75) Inventors: Benjamin S. Barrall, Conshohocken, PA (US); Barclay Ross Davis, Glenmoore, PA (US); Dennis Chien, Chester Springs, PA (US)

(73) Assignee: Synthes USA, LLC, West Chester, PA (US)

( * ) Notice: Subject to any disclaimer, the term of this patent is extended or adjusted under 35 U.S.C. 154(b) by 827 days.

(21) Appl. No.: 11/001,902

(22) Filed: Dec. 1, 2004

(65) Prior Publication Data

US 2006/0116683 A1    Jun. 1, 2006

(51) Int. Cl.
*A61B 17/80* (2006.01)
(52) U.S. Cl. ....................................................... 606/70
(58) Field of Classification Search ................. 606/902, 606/279, 86 B, 915, 70–71, 280–299; 600/300, 600/311, 312, 308; 623/908
See application file for complete search history.

(56) References Cited

U.S. PATENT DOCUMENTS

| | | | |
|---|---|---|---|
| 3,547,114 A | 12/1970 | Haboush | |
| 3,604,414 A | 9/1971 | Borges | |
| 3,606,414 A * | 9/1971 | Haley | 52/714 |
| 3,659,595 A | 5/1972 | Haboush | |
| 3,950,001 A * | 4/1976 | Weigl | 280/618 |
| 4,157,715 A | 6/1979 | Westerhoff | |
| 5,129,903 A | 7/1992 | Luhr et al. | |
| 5,190,544 A * | 3/1993 | Chapman et al. | 606/71 |
| 5,234,431 A | 8/1993 | Keller | |
| 5,344,421 A | 9/1994 | Crook | |
| 5,470,333 A | 11/1995 | Ray | |
| 5,484,439 A | 1/1996 | Olson et al. | |
| 5,531,745 A | 7/1996 | Ray | |
| 5,531,747 A | 7/1996 | Ray | |
| 5,616,142 A | 4/1997 | Yuan et al. | |
| 5,672,177 A | 9/1997 | Seldin | |
| 5,681,313 A | 10/1997 | Diez | |
| 5,728,099 A | 3/1998 | Tellman et al. | |
| 5,827,286 A | 10/1998 | Incavo et al. | |
| 5,842,822 A * | 12/1998 | Everett et al. | 411/339 |
| 5,902,304 A | 5/1999 | Walker et al. | |
| 5,964,762 A | 10/1999 | Biedermann et al. | |

(Continued)

FOREIGN PATENT DOCUMENTS

EP    0 773004 A1    5/1997

(Continued)

OTHER PUBLICATIONS

Spinal Concepts—Ant Cer® (printed from Website on Jun. 25, 2004).

*Primary Examiner*—Thomas C Barrett
*Assistant Examiner*—James L Swiger
(74) *Attorney, Agent, or Firm*—Stroock & Stroock & Lavan LLP

(57) ABSTRACT

A fixation assembly is described comprising at least two plates, one of which may be a contoured plate and one of which may be a securing plate. The contoured plate may have a plurality of teeth, and the securing plate may have a resilient securing element. The teeth may be arranged so that the resilient securing element encounters progressive resistance as the plates are compressed.

8 Claims, 19 Drawing Sheets

U.S. PATENT DOCUMENTS

| | | | |
|---|---|---|---|
| 5,964,763 | A | 10/1999 | Incavo et al. |
| 5,973,223 | A | 10/1999 | Tellman et al. |
| 6,051,007 | A | 4/2000 | Hogendijk et al. |
| 6,126,660 | A | 10/2000 | Dietz |
| 6,277,124 | B1 | 8/2001 | Haag |
| 6,302,883 | B1 | 10/2001 | Bono |
| 6,306,136 | B1 | 10/2001 | Baccelli |
| 6,328,738 | B1 | 12/2001 | Suddaby |
| 6,402,756 | B1 | 6/2002 | Ralph et al. |
| 6,432,108 | B1 | 8/2002 | Burgess et al. |
| 6,471,706 | B1 | 10/2002 | Schumacher et al. |
| 6,645,208 | B2 | 11/2003 | Apfelbaum et al. |
| 6,666,867 | B2 | 12/2003 | Ralph et al. |
| 6,689,134 | B2 | 2/2004 | Ralph et al. |
| 6,699,249 | B2 | 3/2004 | Schlapfer et al. |
| 6,761,721 | B2 | 7/2004 | Burgess et al. |
| 6,852,113 | B2 | 2/2005 | Nathanson |
| 6,926,718 | B1 * | 8/2005 | Michelson ............... 606/247 |
| 6,932,820 | B2 * | 8/2005 | Osman ............... 606/71 |
| 7,033,377 | B2 * | 4/2006 | Miller, III ............... 606/213 |
| 7,399,301 | B2 * | 7/2008 | Michelson ............... 606/71 |
| 2002/0016595 | A1 | 2/2002 | Michelson |
| 2002/0022843 | A1 | 2/2002 | Michelson |
| 2002/0055741 | A1 | 5/2002 | Schlapfer et al. |
| 2002/0111630 | A1 | 8/2002 | Ralph et al. |
| 2002/0143336 | A1 | 10/2002 | Hearn |
| 2002/0161374 | A1 | 10/2002 | Cohen et al. |
| 2002/0183754 | A1 | 12/2002 | Michelson |
| 2002/0183755 | A1 | 12/2002 | Michelson |
| 2002/0183756 | A1 | 12/2002 | Michelson |
| 2002/0183757 | A1 | 12/2002 | Michelson |
| 2002/0188296 | A1 | 12/2002 | Michelson |
| 2003/0060828 | A1 | 3/2003 | Michelson |
| 2003/0074001 | A1 | 4/2003 | Apfelbaum et al. |
| 2003/0083694 | A1 | 5/2003 | Miller, III |
| 2003/0114856 | A1 | 6/2003 | Nathanson et al. |
| 2003/0130661 | A1 | 7/2003 | Osman |
| 2003/0153920 | A1 | 8/2003 | Ralph et al. |
| 2003/0167059 | A1 | 9/2003 | Young |
| 2003/0212399 | A1 | 11/2003 | Dinh et al. |
| 2003/0229348 | A1 | 12/2003 | Sevrain |
| 2004/0019353 | A1 | 1/2004 | Freid et al. |
| 2004/0092939 | A1 * | 5/2004 | Freid et al. ............... 606/79 |
| 2004/0097938 | A1 | 5/2004 | Alleyne |
| 2004/0102778 | A1 | 5/2004 | Huebner et al. |
| 2004/0106924 | A1 | 6/2004 | Ralph et al. |
| 2004/0127903 | A1 | 7/2004 | Schlapfer et al. |
| 2004/0204712 | A1 * | 10/2004 | Kolb et al. ............... 606/69 |
| 2004/0210219 | A1 | 10/2004 | Bray |
| 2004/0220566 | A1 | 11/2004 | Bray |
| 2005/0043732 | A1 * | 2/2005 | Dalton ............... 606/61 |

FOREIGN PATENT DOCUMENTS

| | | |
|---|---|---|
| EP | 0 780095 A1 | 6/1997 |
| EP | 0 904740 A2 | 3/1999 |
| EP | 0 829240 A1 | 10/1999 |
| EP | 1205154 A2 | 5/2002 |
| FR | 2796829 A1 | 2/2001 |
| JP | 2063455 A | 7/1992 |
| WO | WO 9614802 A1 | 5/1996 |
| WO | WO 9720512 A1 | 5/1997 |
| WO | WO 9632072 A1 | 6/1997 |
| WO | WO 9811837 A1 | 10/1999 |
| WO | WO 9904718 A1 | 10/2001 |
| WO | WO 03037201 A1 | 5/2003 |
| WO | WO 03063714 A2 | 8/2003 |
| WO | WO 03071966 A1 | 9/2003 |

* cited by examiner

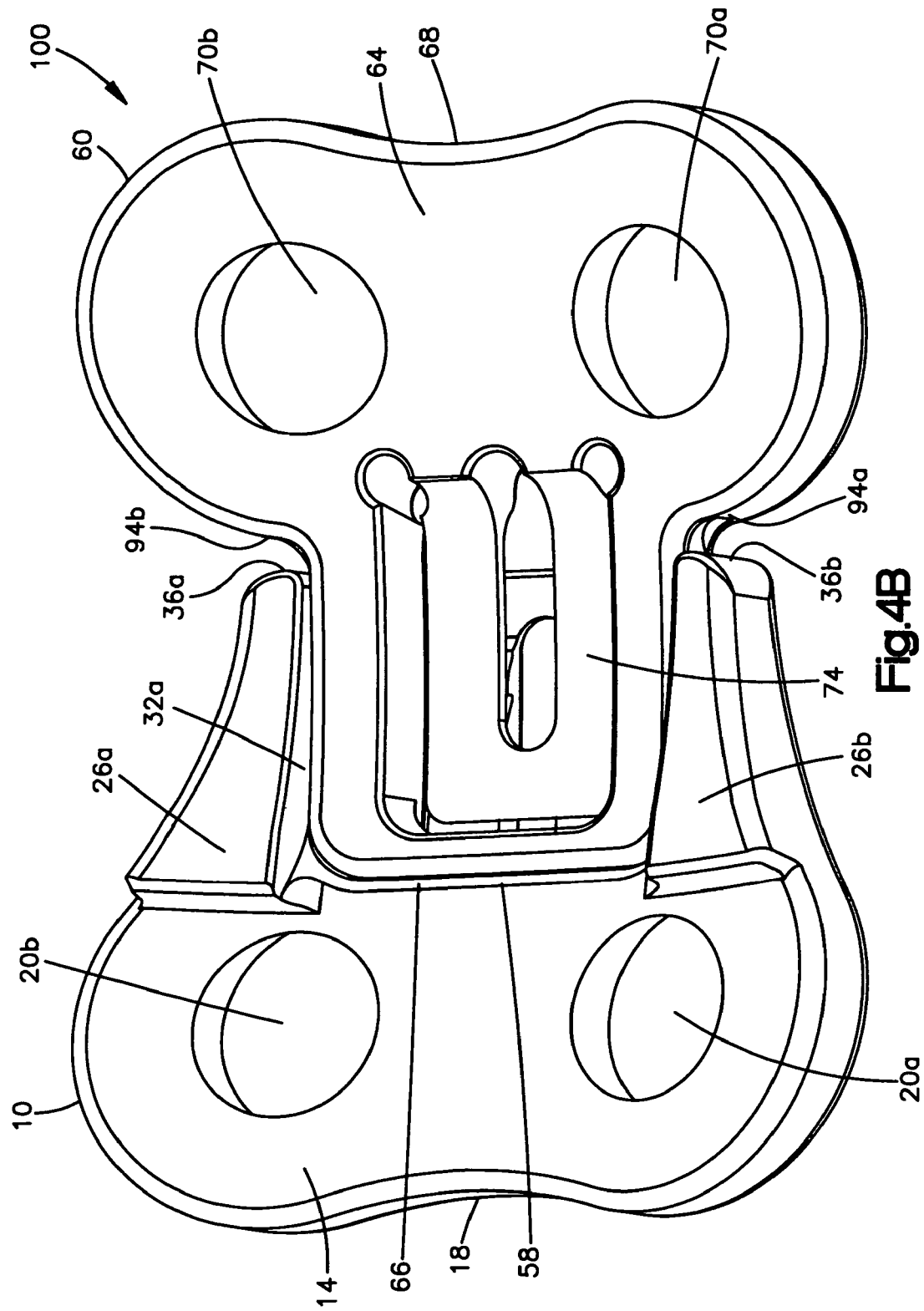

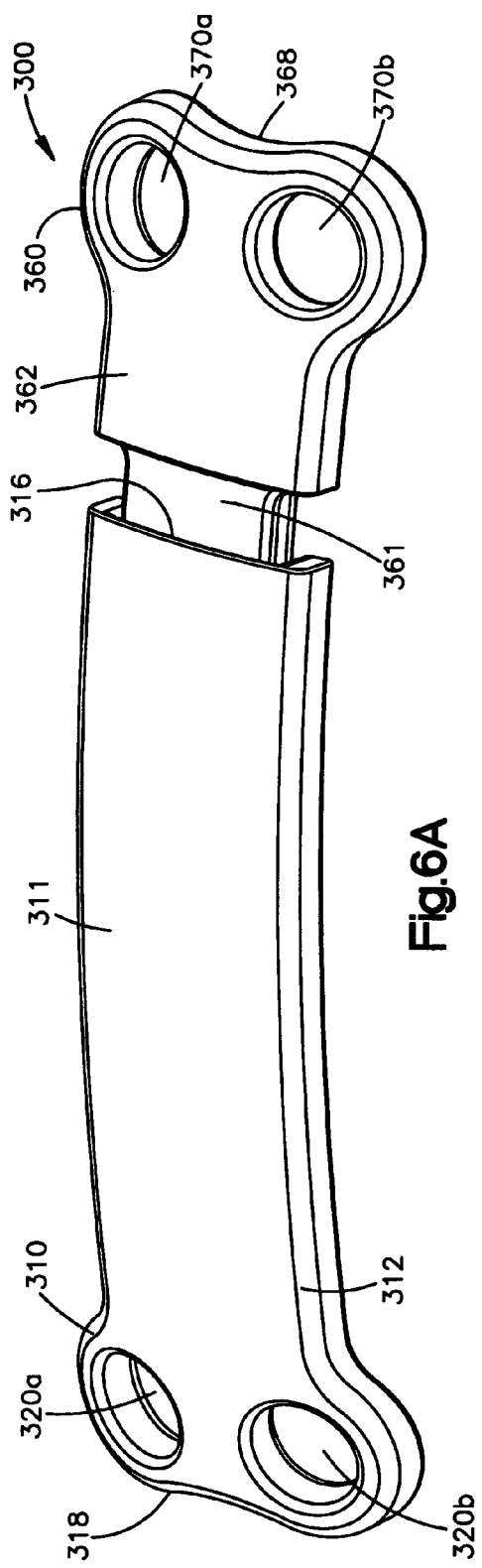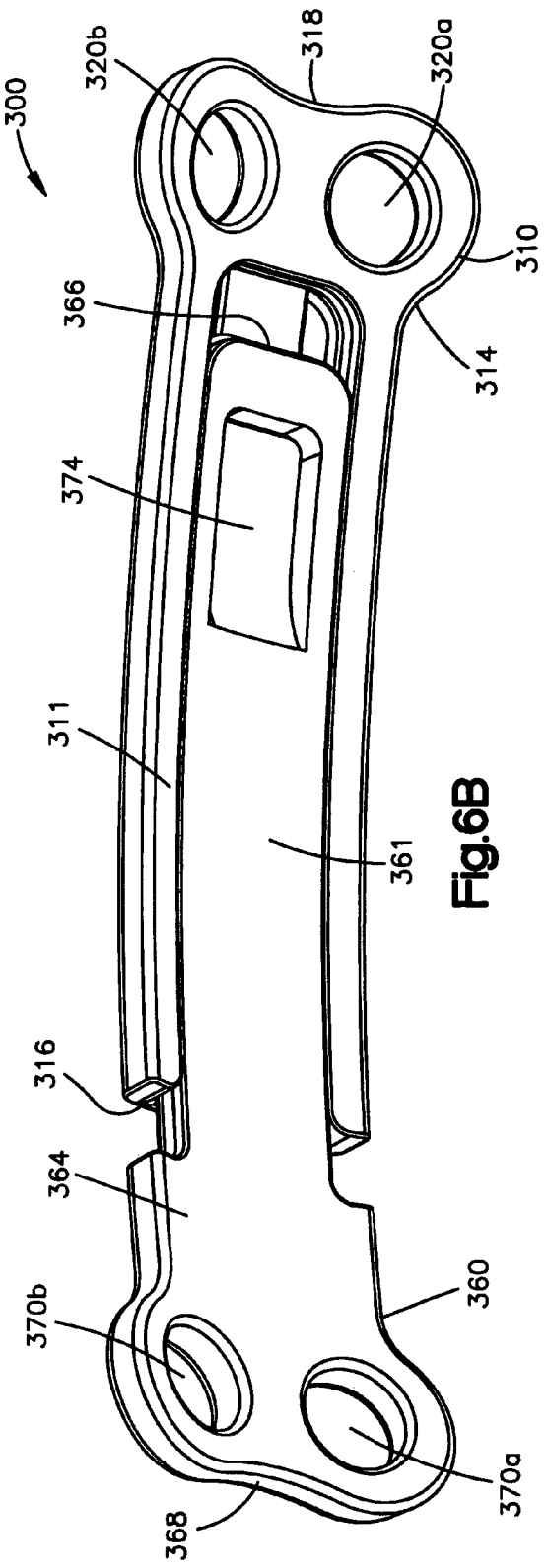

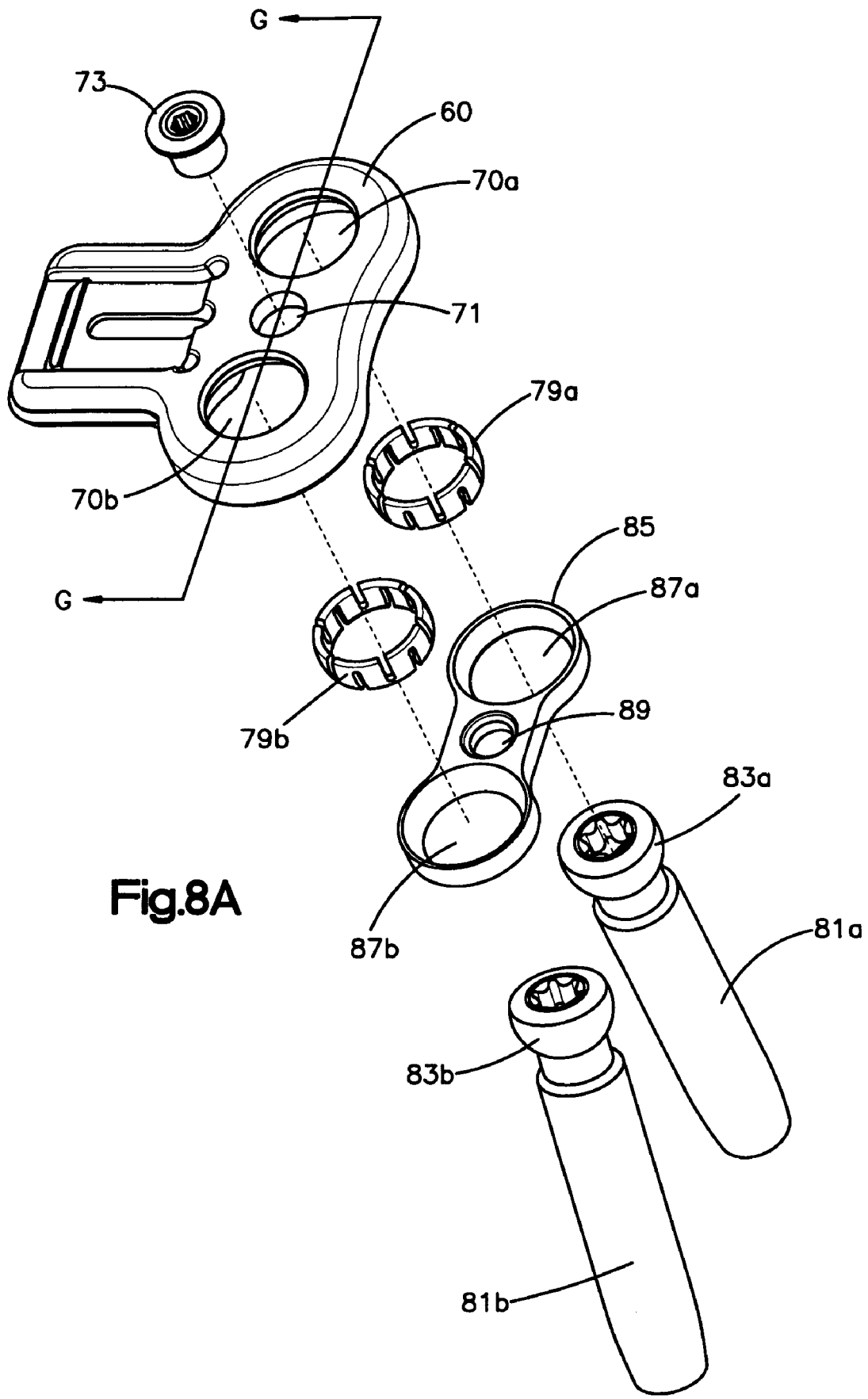

UNIDIRECTIONAL TRANSLATION SYSTEM FOR BONE FIXATION

FIELD OF THE INVENTION

The present invention is related to a fixation system. More particularly, the invention is related to a fixation system consisting of a translational plate system with a plurality of fastener holes.

BACKGROUND OF THE INVENTION

Orthopedic fixation devices such as plates are frequently coupled to bone with fasteners inserted through plate holes. It is known that securing such fasteners to the bone plate, for example through the use of expansion-head screws, can decrease the incidence of loosening of the fixation assembly post-operatively. It is also known that a bushing may be disposed in each plate hole to receive the fastener to permit polyaxial movement so that the fastener may be angulated at a surgeon-selected angle. However, polyaxial movement of fasteners through set plate hole locations only increases attachment alternatives of the fasteners themselves. The plate holes remain fixed in relation to each other and to the longitudinal axis of the plate.

Typically, a spinal fixation plate is applied to the anterior side of the affected vertebrae to span at least one affected disc space or vertebra (i.e. one in which at least a portion of the disc has been removed and a spinal fusion spacer has been inserted). The plate is fixed to the vertebrae using bone screws and acts to keep the vertebrae generally aligned during the initial period following fixation in which fusion of the spacer to the adjacent vertebrae occurs. The plate also may act to prevent the spacer from being expelled from the disc space during this initial period.

Where a spinal fusion spacer is implanted between a pair of vertebrae to be fused, the spacer rests on the endplates of the vertebrae. The outer circumference of the end plates comprises hard cortical bone and thus provides the best surface upon which to seat the spacer. The center portion of the endplates comprises a thin cortical bone shell overlying a core of softer cancellous bone. Most, if not all, of the spacer contact surface, however, may be located in this center portion.

Subsequent to placement of the spacer, the surgeon typically compresses the disc space by pressing the adjacent vertebrae together. This compression ensures a good engagement between the spacer and the endplates, increasing the chances that fusion will occur. Often in the period immediately following surgery, the spacer may subside slightly into the under-portion of the endplates, or the space between the vertebral endplates may decrease due to graft resorption (in the case of allograft spacers).

Where a rigid fixation plate is used to connect the vertebrae, this subsidence may tend to shift more of the spinal load to the plate than is desirable. Such load shifting can also occur due to inaccuracies in installing the plate to the vertebrae. In extreme circumstances, this load shifting can result in non-fusion of the spacer to the vertebra, since firm compression between the spacer and the vertebrae is one factor contributing to successful fusion.

Accordingly, there exists a need for a fixation system which provides the desired support to the vertebrae to be fused, and which allows limited compression of the vertebrae with respect to at least a portion of the plate, thereby limiting the undesirable effects of load shielding by the plate due to graft subsidence caused by settling or normal forces experienced in the spinal column. Promoting fusion of the adjacent vertebrae may thus accomplished.

Translation plates which compensate for this subsidence by providing the aforementioned benefits of a rigid fixation plate (general vertebral alignment, and prevention of spacer expulsion), while for controlled compression of the vertebrae to compensate for post-surgical subsidence, may be desirable. This compensation may permit the majority of the spinal column load to be borne by the spacer rather than the plate.

There further exists a need for a fixation system that allows for intraoperative compression by the surgeon. Often, a surgeon may wish to provide an initial level of compression on affected vertebrae after a graft has been inserted, but before the incision is closed. This initial compression can provide a snug fit for a graft between adjacent vertebrae, and therefore decrease the period necessary for effective fusion.

SUMMARY OF THE INVENTION

A fixation assembly is described having a longitudinal axis comprising: a first plate having at least one fastener hole configured to receive a fastener, and a plurality of rows of teeth; a second plate having at least one fastener hole configured to receive a fastener, and a resilient securing element engageable with the teeth to couple the plates together; wherein the second plate is movable along the longitudinal axis with respect to the first plate; and wherein the compressive force necessary to engage the resilient element with subsequent rows of teeth increases as the second plate moves farther along the longitudinal axis.

The assembly may be unidirectional. The assembly may be allowed to translate in situ. The assembly may be allowed to translate after at least one fastener is received in at least one fastener hole in the first and second plate, wherein the fasteners are further inserted into bone segments.

The assembly may further comprise a first fastener inserted into a fastener hole in the first plate, and a second fastener inserted into a fastener hole in the second plate. The first fastener may be inserted into a first bone segment and the second fastener may be inserted into a second bone segment. The first and second bone segments may be adjacent vertebrae.

The assembly may further comprise a third plate.

A first row of teeth may have a first elevation, and a second row of teeth may have a second elevation, wherein the second elevation is greater than the first elevation. The first plate may comprise at least three rows of teeth. The axial force required for the resilient securing element to engage a second row of teeth may be less than the axial force required for the resilient securing element to engage to a third row of teeth.

At least one fastener may be a bone screw. At least one bone screw may be self-drilling. At least one bone screw may be self-tapping. At least one bone screw may be able to toggle within a fastener hole.

The first and second plate may each further comprise a window.

Another fixation assembly is described comprising: a first plate having at least one fastener hole configured to receive a fastener; a second plate having at least one fastener hole configured to receive a fastener; wherein the first plate is coupled to and translatable with respect to the second plate; wherein the assembly has a plurality of compressed lengths; and wherein a greater axial force is required to compress the assembly to increasingly smaller compressed lengths.

Another fixation assembly is described comprising: a first plate having at least one fastener hole configured to receive a fastener; a second plate having a least one fastener hole configured to receive a fastener; wherein the first plate and the second plate are engageable in a first compressed position and a second compressed position; wherein the length of the assembly is greater in the first compressed position than that of the second compressed position; and wherein a progressively greater axial force is required to compress the first plate and the second plate from the first compressed position to the second compressed position, than from a non-engaged position to the first compressed position.

Another fixation assembly is described comprising a first plate having at least one fastener hole configured to receive a fastener; a second plate having a least one fastener hole configured to receive a fastener; wherein the first plate has at least a first row of teeth and at least a second row of teeth, the first row of teeth having a first height and the second row of teeth having a second height; wherein the second plate has a resilient securing element; and wherein the second height is greater than the first height.

A method for fixating a plurality of bone segments is described, comprising the steps of: (a) providing a fixation assembly comprising a first plate having at least one bone fastener hole, and at least a first row of teeth and a second row of teeth; and a second plate having at least one bone fastener hole, and a resilient securing element; (b) positioning the assembly adjacent to a desired body site; (c) attaching the first plate to a first bone segment with at least one bone fastener, and the second plate to a second bone segment with at least one bone fastener; and (d) allowing the assembly to translate in situ.

The assembly of step (a) may be in a first compressive condition. The assembly may be allowed to translate to a second compressive condition in situ.

The method may further comprise the step of compressing the assembly manually. The step of manual compression may be performed by a surgeon. The step of manual compression may be performed using a tool. The method may further comprise the step, inserted before step (a), of making an incision in a patient's body, and providing access to a desired body site. The method may further comprise the step of closing the incision.

Another method is described for fixating a plurality of bone segments, comprising the steps of: (a) providing a fixation assembly comprising a first plate having at least one bone fastener hole configured to receive a first bone fastener, and at least a first and second row of teeth; and a second plate having at least one bone fastener hole configured to receive a second bone fastener, and a resilient securing element; (b) inserting the first bone fastener into a first bone segment; and inserting the second bone fastener into a second bone segment; (c) engaging the first plate with the first bone fastener and engaging the second plate with the second bone fastener; (d) placing the assembly in a first compressed condition; and (e) allowing the assembly to translated in situ.

Another method is described for fixating a plurality of bone segments, comprising the steps of (a) attaching a first plate to a first bone segment with at least one bone fastener, the first plate having at least a first and second row of teeth; (b) attaching a second plate to a second bone segment with at least one bone fastener, the second plate having a resilient securing element; (c) engaging the first and second plate in a first compressive position; (d) allowing the first and second plate to shift to a second compressive position in situ.

BRIEF DESCRIPTION OF THE DRAWINGS

While preferred features of the present invention may be disclosed in the accompanying illustrative, exemplary drawings, for the purposes of description, the invention as defined by the claims should be in no way limited to such preferred features or illustrative and exemplary drawings, wherein:

FIG. 4B is another perspective view of the assembly of FIG. 4A;

FIG. 6A is a perspective view of another embodiment of a fixation assembly in a corpectomy arrangement;

FIG. 6B is another perspective view of the plate of FIG. 6A;

FIG. 8A is an exploded view of another embodiment of a fastener-securing assembly for use with a plate;

DETAILED DESCRIPTION OF THE INVENTION

The plates described herein may be used in spinal fusion procedures in which a damaged or diseased disc (or part of a disc) is removed from between a pair of vertebrae and a spinal fusion spacer is placed between the vertebrae. The plates may be applied to an anterior portion of the affected vertebrae to span the affected disc space, and may be fixed to the vertebrae using bone screws. The plate may function to maintain the vertebrae aligned during the initial period following fixation in which fusion of the spacer to the adjacent vertebrae occurs. The plate may also function to share some of the axial spinal load applied to the fusion spacer to prevent extreme subsidence of the spacer into the vertebral body, such as where the patient has poor bone quality. The plates may also act to prevent the spacer from being expelled from the disc space during the initial post-operative period.

The plates may be used for single level (i.e. one-disc) or multiple-level (i.e. multiple disc) fusion procedures. Some embodiments may be used for corpectomy procedures, in which at least a portion of a vertebral body is removed. Single level plates generally may have two pairs of bone screw holes, while the multi-level plates generally may have three or more pairs of holes. While the plates herein are described with reference and application to the spine, it will be appreciated that features of the plates and the plates may have other applications, and can be applied to other bones and/or parts of the skeleton.

Figure 1A:
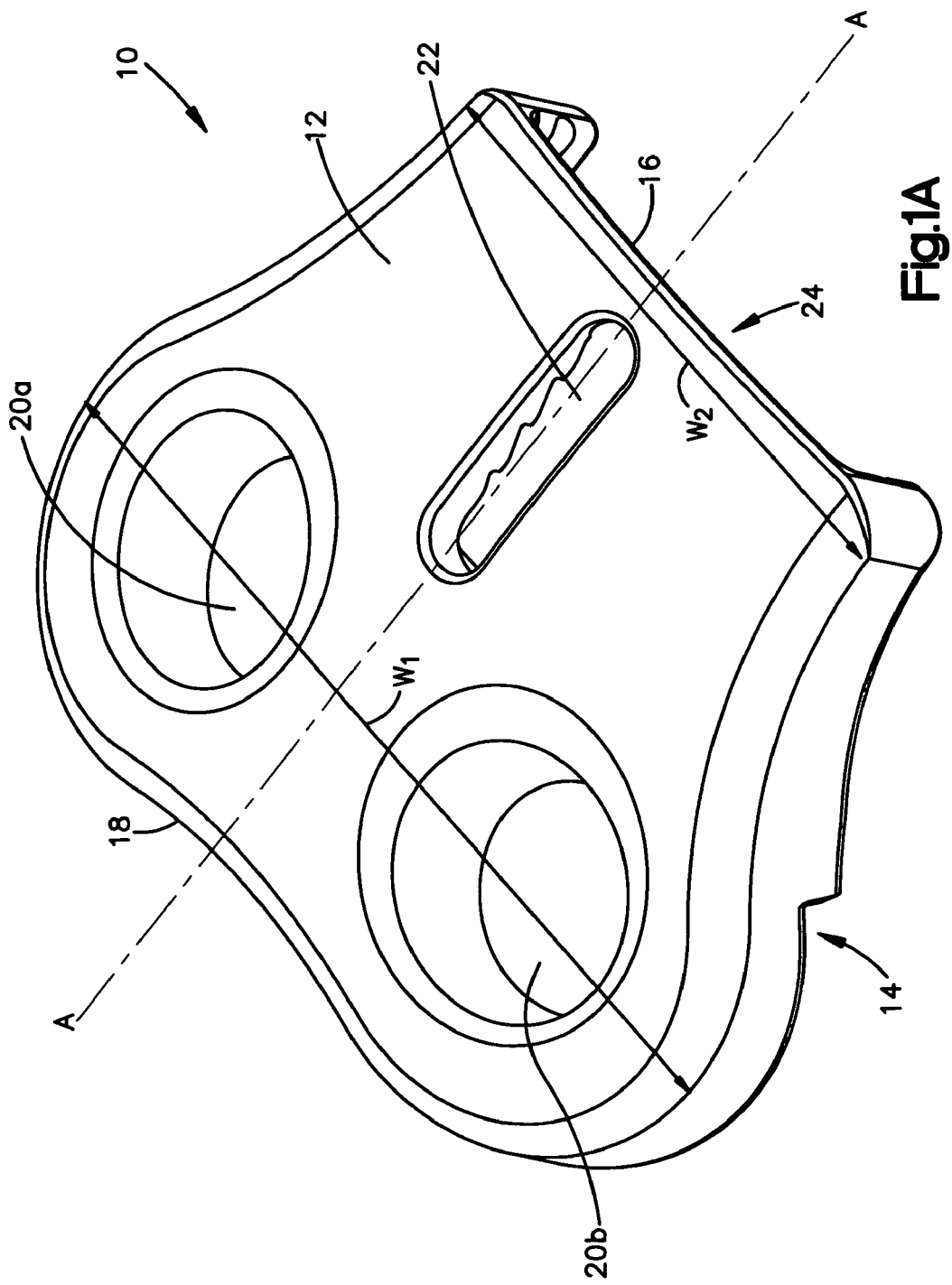
FIG. 1A is a perspective view of an embodiment of a contoured plate.

FIGS. 1A-4B show an embodiment of a one-level assembly, and the components thereof. FIGS. 1A-1B show views of a contoured plate 10, which may have an upper surface 12, a lower surface 14, and a longitudinal axis A-A. Contoured plate 10 may also have an engaging end 16 and a fastening end 18. The embodiment of contoured plate 10 shown in FIGS. 1A-1B includes two fastener holes 20a, 20b. Fastener holes 20a, 20b may be configured to receive at least a portion of a bone fastener (see, e.g., FIGS. 7A-8B, discussed infra), which may be inserted into a bone segment, such as a vertebral body. Upper and lower surfaces 12, 14 may be generally curved surfaces. Lower surface 14 may have a radius of curvature $R_1$ at or near the fastening end 18. Plate 10 may also have a fastening width $W_1$, which may be from about 2 mm to about 50 mm, and an engaging width $W_2$, which may be from about 1 mm to about 50 mm.

Plate 10 may also have a window 22 extending from the upper surface 12 through the lower surface 14. The window 22 may be located near the engaging end 16 of the plate 10. Window 22 may be beneficial to reduce the overall weight of plate 10, and/or provide visual access to a disc space below the plate 10 when implanted into a patient's body. Window 22 may also provide access to tab 74 of securing plate 60 (discussed infra in detail), whereby a surgeon may use a tool or other instrument to manually urge the tab 74. This procedure may serve as a way for a surgeon to reduce the amount of compression intraoperatively, as the surgeon may access tab 74 via window 22 sufficient to bend tab 74 and release tab 74 from a row of teeth.

Plate 10 may also have a recess 24, located at or near the engaging end 16. Recess 24 may be appropriately shaped and sized to receive at least a portion of another plate element or desired structure, such as a securing plate 60, discussed infra in relation to FIGS. 2A-2B. Recess 24 may extend substantially over the engaging width $W_2$ of plate 10.

Figure 1B:
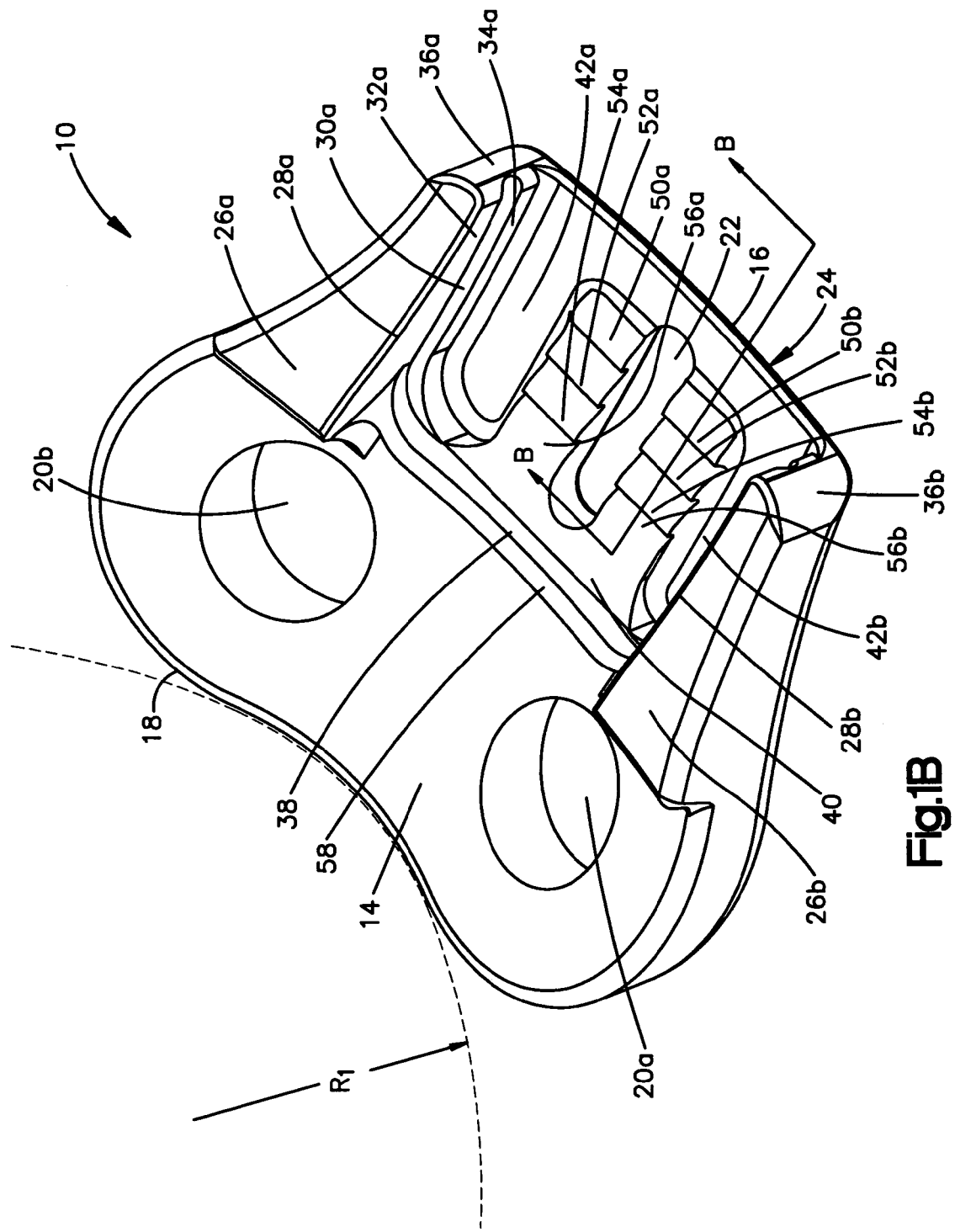
FIG. 1B is another perspective view of the plate of FIG. 1A.

FIG. 1B shows the lower surface 14 of plate 10 in more detail. Lower surface 14 may have several features that may provide for various engagement options with another plate. Recess 24 may be flanked by raised portions 26a, 26b, which may be beneficial to allow the recess 24 to have sufficient depth to receive a plate. The boundary of the recess 24 may generally be raised edges 28a, 28b, from which the raised portions 26a, 26b may fall off into recess 24. Alternatively, it may be advantageous for the plate 10 to not have any raised portions 26a, 26b at all. Whether or not to use a plate 10 with raised portions 26a, 26b may depend at least in part on the surface features of the affected vertebrae. Raised edges 28a, 28b may extend to side ledges 30a, 30b (not shown in FIG. 1B), which may engage a slidably received plate. In between raised edges 28a, 28b and side ledges 30a, 30b, there may be side stop surfaces 32a, 32b (not shown in FIG. 1B), which may serve to control the transverse sliding of a received plate with respect to the longitudinal axis A-A of plate 10, and may thereby maintain the correct orientation of received plate. Side ledges 30a, 30b may terminate in engaging edges 34a, 34b (not shown in FIG. 1B). A combination of these elements may assist in controlling the transverse sliding movement of a received plate (such as securing plate 60, discussed infra).

Several features of plate 10 may also serve to control the longitudinal sliding movement of a received plate near or at recess 24. Plate 10 may have end stop surfaces 36a, 36b located at engaging end 16, which may engage a corresponding surface on a received plate (i.e. end stop surfaces 94a, 94b of securing plate 60, discussed infra). Within recess 24, plate 10 may also have an engaging stop surface 38 located near or at the end of recess 24. There may also be a curved stop surface 40 and angled stop surface 58 located adjacent to engaging stop surface 38. Stop surfaces 36a, 36b, 38, 40, and 58 may therefore, alone or in combination, assist in preventing a received plate from extending too far into plate 10, and may therefore set a minimum length of a fixation assembly including plate 10 (see, e.g., FIGS. 4A-4B).

Plate 10 may provide primary sliding surfaces 42a, 42b for sliding engagement with a received plate. Preferably, primary sliding surfaces 42a, 42b should correspondingly to respective sliding surface of a received plate to ensure a sufficiently secure fit between plate 10 and a received plate.

Plate 10 may also have a series of teeth along the lower surface 14 within recess 24. The embodiment of plate 10 shown in FIG. 1B contains three sets of two teeth 50a, 50b, 52a, 52b, and 54a, 54b, along with one set of ramped surfaces 56a, 56b. It is expressly contemplated that a contoured plate 10 may have any suitable number of teeth and/or ramped surfaces to provide desired variable engagement locations for plate 10 and a received plate. For instance, plate 10 may have two sets of teeth and two sets of ramped surfaces. Further, plate 10 may have four sets of teeth and no ramped surfaces. Teeth and/or ramped surfaces may or may not exist in sets. Teeth and/or ramped surfaces may exist in sets of two, three, or more. Other combinations will be appreciated by those skilled in the art.

Figure 1C:
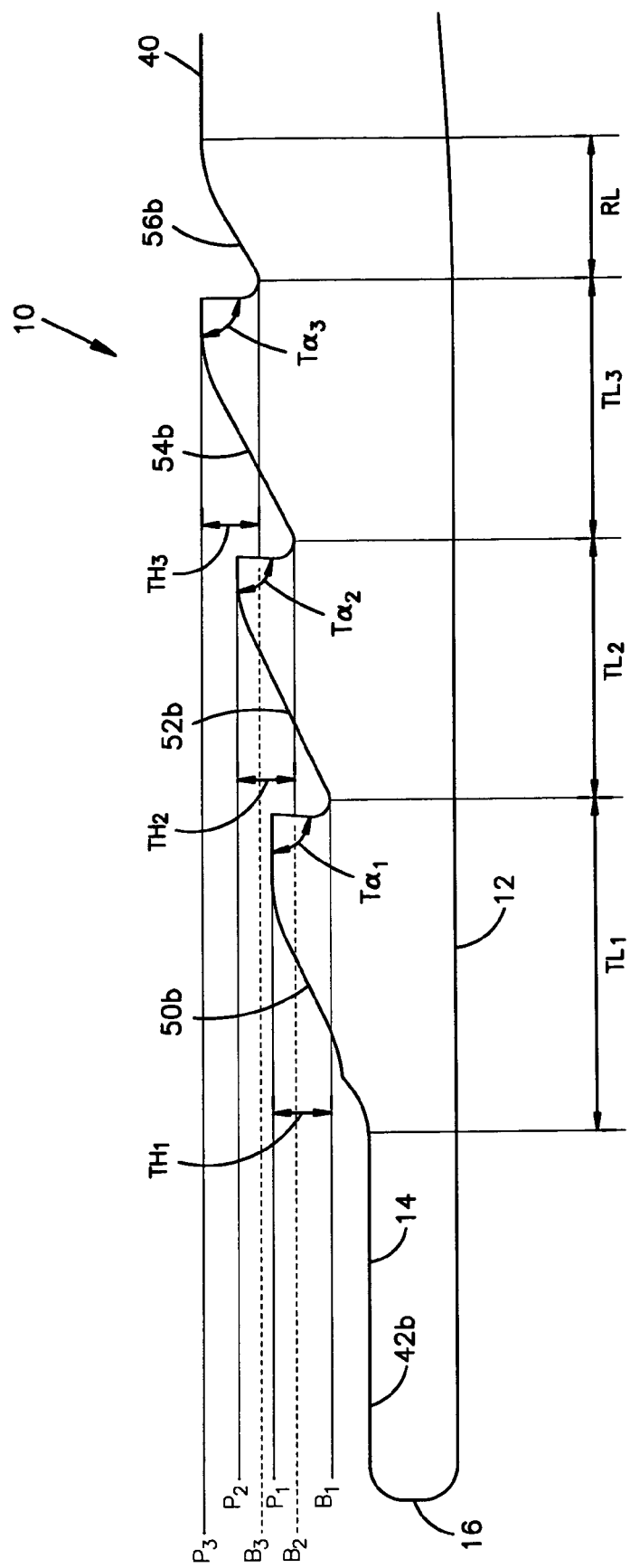
FIG. 1C is a partial cross-sectional view of the plate of FIG. 1B taken along the line B-B.

The teeth and ramped surfaces of FIG. 1B are shown in more detail in FIG. 1C, which is a partial cross-sectional view of plate 10 taken along the line B-B. In this embodiment, the individual teeth of each set are substantially identical to the other teeth within its respective set. Therefore, first tooth 50a is substantially identical to first tooth 50b, which comprise first set of teeth 50a, 50b. It should be noted that it may or may not be preferable to have sets of teeth comprised of individual teeth that are substantially identical.

First set of teeth 50a, 50b may have a length $TL_1$, a height $TH_1$, and may form an inclusive angle $T\alpha_1$. $TL_1$ may be from about 0.1 mm to about 3 mm, $TH_1$ may be from about 0.1 mm to about 3 mm, and $T\alpha_1$ may be from about 30 degrees to about 90 degrees. Similarly, second set of teeth 52a, 52b may have a length $TL_2$, a height $TH_2$, and may form an inclusive angle $T\alpha_2$. $TL_2$ may be from about 0.1 mm to about 3 mm, $TH_2$ may be from about 0.1 mm to about 3 mm, and $T\alpha_2$ may be from about 30 degrees to about 90 degrees. Further, third set of teeth 54a, 54b may have a length $TL_3$, a height $TH_3$, and may form an inclusive angle $T\alpha_3$. $TL_3$ may be from about 0.1 mm to about 3 mm, $TH_3$ may be from about 0.1 mm to about 3 mm, and $T\alpha_3$ may be from about 30 degrees to about 90 degrees.

FIG. 1C shows a partial cross-sectional view of the plate 10 of FIG. 1B taken along the line B-B, and viewed from the far side of plate 10. As can been seen from FIG. 1C, each tooth may have a base elevation and a peak elevation. In particular, first tooth 50a may have a base elevation $B_1$ and a peak elevation $P_1$, second tooth 52a may have a base elevation $B_2$ and a peak elevation $P_2$, and third tooth 54a may have a base elevation $B_3$ and a peak elevation $P_3$. In the embodiment of FIG. 1C, base elevations $B_1$, $B_2$, $B_3$ rise progressively from the first tooth 50b, to the second tooth 52b, to the third tooth 54b. Similarly, peak elevations $P_1$, $P_2$, $P_3$ may rise progressively from first tooth 50b, to the second tooth 52b, to the third tooth 54b. The progressive rise in base and peak elevations in the direction of the first tooth 50b toward the third tooth 54b may be advantageous to provide progressive resistance for an engaging element (such as tab 74 of securing plate 60, discussed in detail infra), as a received plate is urged further into recess 24 of plate 10. This relationship is discussed below in greater detail in relation to the assemblies of FIGS. 3A-4B.

In the embodiment shown in FIG. 1C, teeth heights $TH_1$, $TH_2$, $TH_3$ are substantially equal, and teeth angles $T\alpha_1$, $T\alpha_2$, $T\alpha_3$ are also substantially equal. However, teeth $TL_1$, $TL_2$, $TL_3$ lengths are not substantially equal, which may be an incidental result of the relationships between base elevations $B_1$, $B_2$, $B_3$ and peak elevations $P_1$, $P_2$, $P_3$ of plate 10. While the teeth heights and angles shown in FIG. 1C are substantially identical, and the teeth lengths are substantially different, it may be preferable to have teeth with different heights, lengths, and/or angles within the recess 24 of plate 10. For instance, teeth may have progressively smaller or larger heights, lengths, and/or angles, which may provide further increased or decreased resistance to a received plate. It is expressly contemplated that all three aspects of the teeth (length, height, and inclusive angle) may be varied by those skilled in the art to provide a desired engagement structure within recess 24 of plate 10 for engagement with a received plate.

The embodiment of FIG. 1C also shows first tooth 50b having a slightly different shape than that of second and third teeth 52b, 54b. Such variations in shape may be beneficial to promote increased or decreased progressive resistance, and/or to provide a more secure fit for a desired engagement structure, such as a tab 74. It is expressly contemplated that the shape of the first, second, and third set of teeth 50a, 50b, 52a, 52b, 54a, 54b, in addition to ramped surfaces 56a, 56b, may be varied by those skilled in the art. It may be beneficial for all sets to teeth to have the same shape, or vary the shapes of the teeth.

FIG. 1C also shows a ramped surface representative of both ramped surfaces 56a, 56b, which may generally follow the last row of teeth (in this case, third set of teeth 54a, 54b). Ramped surfaces 56a, 56b may not provide a level of resistance equal to that provided by teeth 50a, 50b, 52a, 52b, 54a, 54b, but may provide some level of resistance before a received plate reaches curved stop surface 40. Ramped surface may have a length RL.

Figure 2A:
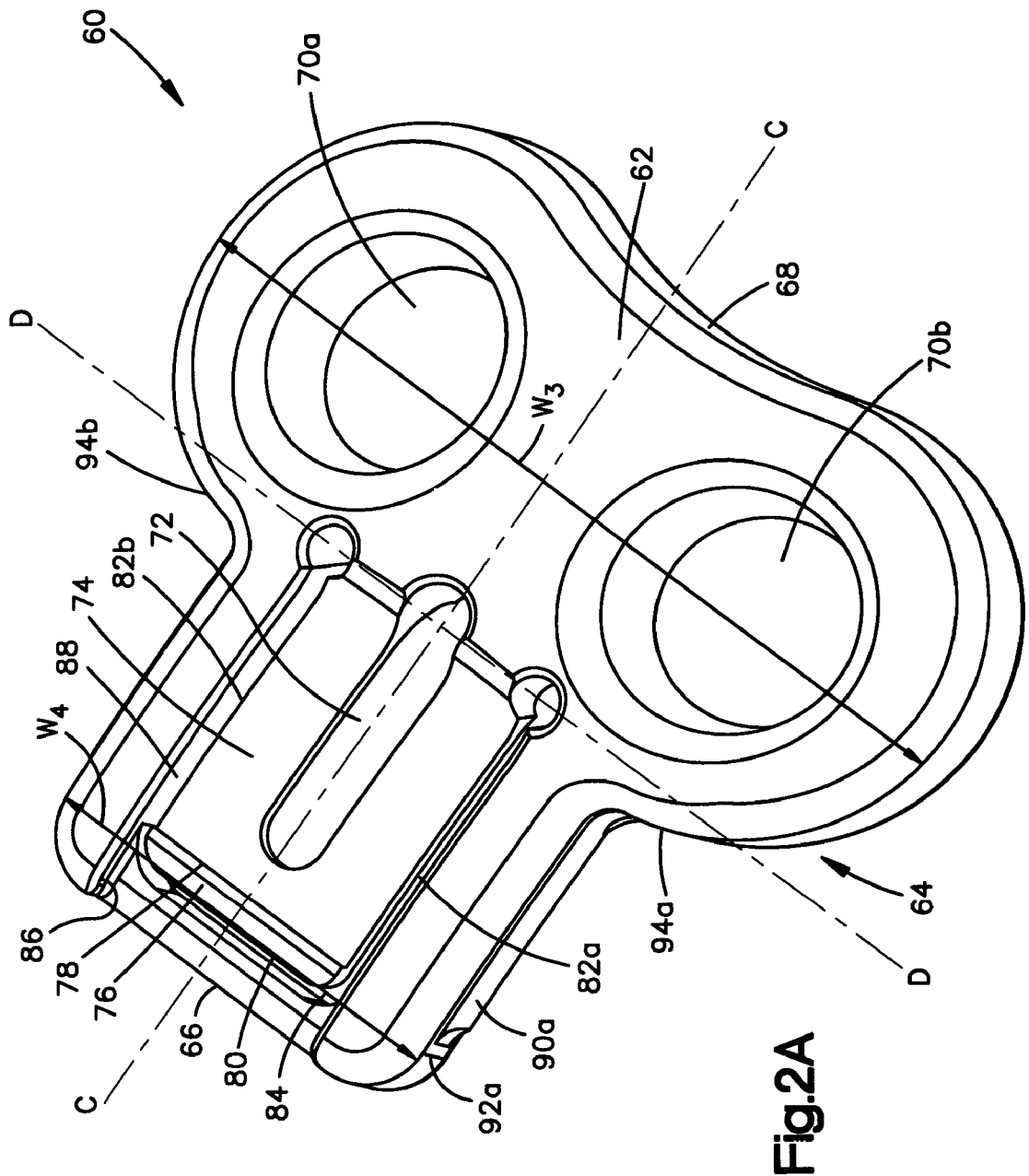
FIG. 2A is a perspective view of an embodiment of a securing plate.
Figure 2B:
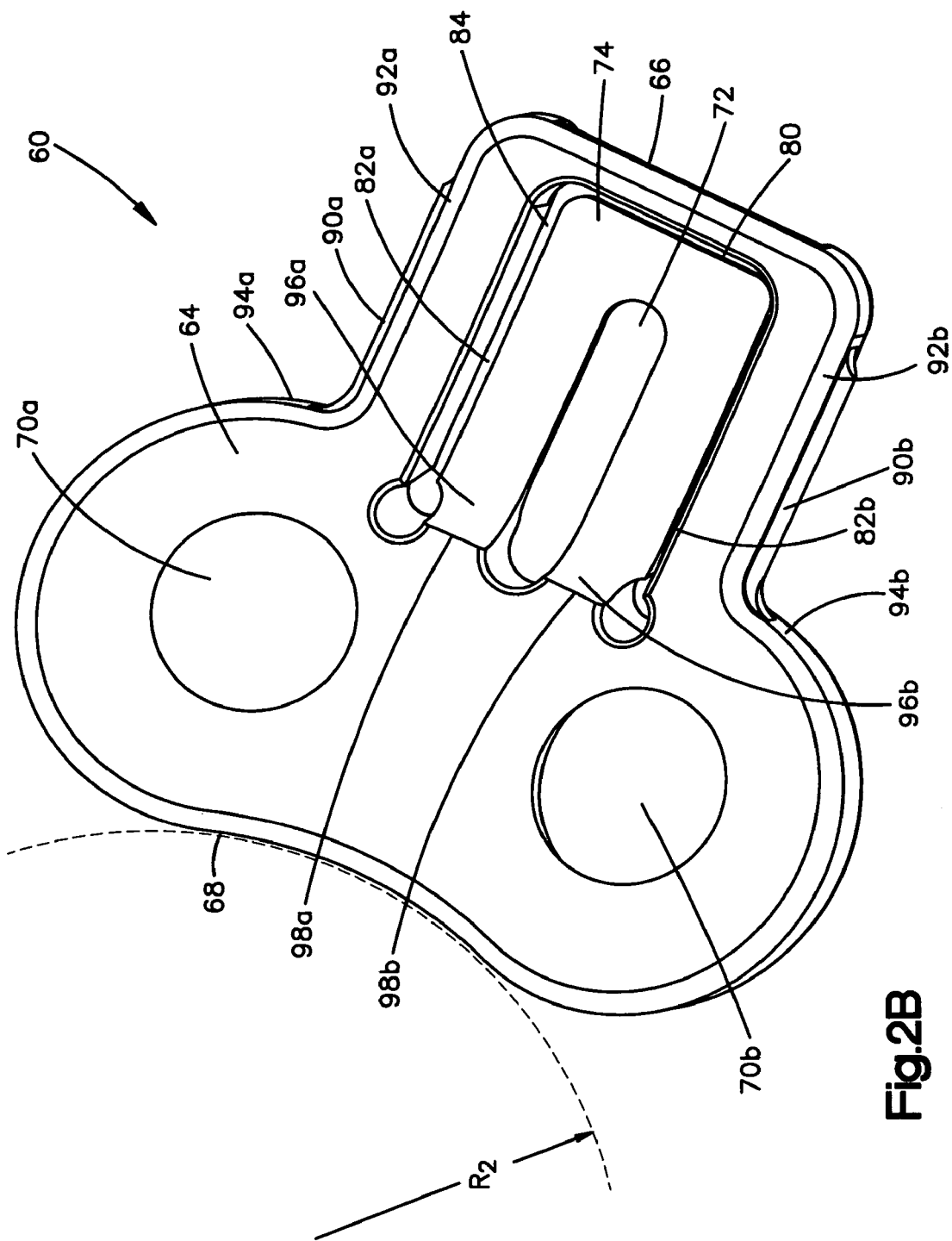
FIG. 2B is another perspective view of the plate of FIG. 2A.

FIGS. 2A-2B show views of a securing plate 60, which may have an upper surface 62, a lower surface 64, and a longitudinal axis C-C. Securing plate 60 may also have an engaging end 66 and a fastening end 68. Like contoured plate 10, the embodiment of securing plate 60 shown in FIGS. 2A-2B include two fastener holes 70a, 70b. Fastener holes 70a, 70b may be configured to receive at least a portion of a bone fastener (see, e.g., FIGS. 7A-8B, discussed infra), which may be inserted into a bone segment, such as a vertebral body. Upper and lower surfaces 62, 64 may be generally curved surfaces. Lower surface 64 may have a radius of curvature $R_2$ at or near the fastening end 68. Plate 60 may also have a fastening width $W_3$, which may be from about 2 mm to about 50 mm, and an engaging width $W_4$, which may be from about 1 mm to about 50 mm.

Plate 60 may also have a window 72 extending from the upper surface 62 through the lower surface 64. The window 72 again may be located near the engaging end of the plate 60. Window 72 may be beneficial to reduce the overall weight of plate 60, and/or provide visual access to a disc space below the plate 60 when implanted into a patient's body. As seen in FIGS. 3A-4B, windows 22 and 72 may align when plates 10 and 60 engage.

A portion of securing plate 60 may be configured to engage contoured plate 10, and plate 60 may contain several features for engagement. Plate 60 may have a securing element 74, which may have an enlarged tab 76 and an engaging ridge 78. Securing element 74 may also have a end surface 80, and side surfaces 82a, 82b. Generally, securing element 74 may be a resilient structure that is deflectable between a range of positions to engage at least one corresponding structure on another plate. In the case of contoured plate 10, securing element 74 may be designed to engage a series of teeth or ramped surface of plate 10 when securing plate 60 is inserted into recess 24. When engaging teeth, the engaging ridge 78 may provide a sufficient contour to engage such teeth, as shown in FIGS. 3A-4B. Securing element may be deflectable around axis D-D. Securing element 74 may be separated from a portion of plate 60 by channel 84, leaving end surface 80 and side surfaces 82a, 82b exposed. This arrangement may allow for increased flexibility of the securing element 74.

Figure 3A:
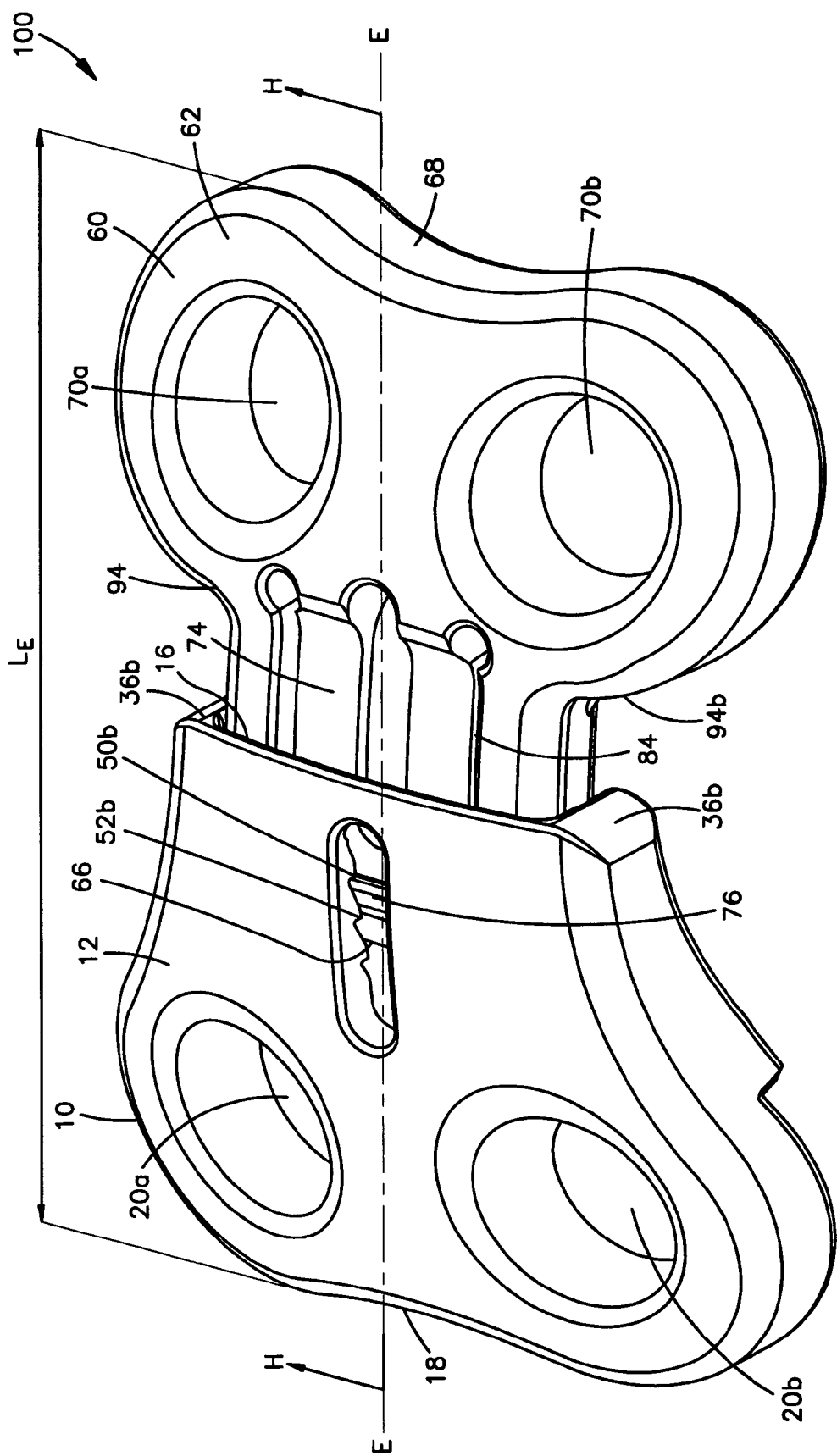
FIG. 3A is a perspective view of an embodiment of a one-level fixation assembly having a contoured plate and a securing plate, and in an expanded position.
Figure 3B:
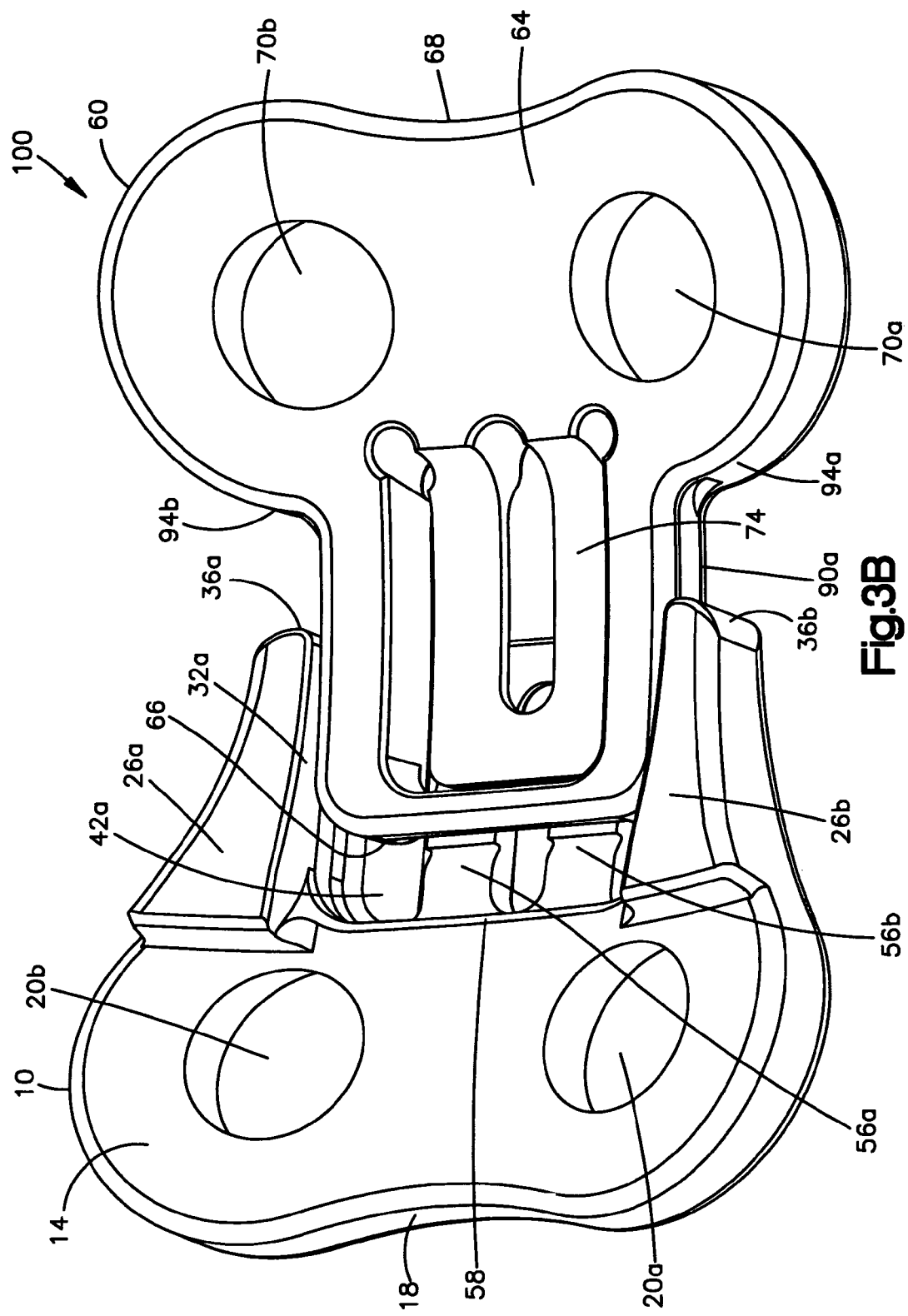
FIG. 3B is another perspective view of the assembly of FIG. 3A.

At and/or near the engaging end of the 66, plate 60 may have a leading groove 86, which may engage a sidewall of the primary sliding surface 42 (see FIG. 3B). Inner surface 88 may engage the primary sliding surface 42 in a similar manner. Plate 60 may also have protrusions 90a, 90b located on sliding side surfaces 92a, 92b disposed between upper and lower surfaces 62, 64. Protrusions 90a, 90b and sliding side surfaces 92a, 92b may engage side ledges 30a, 30b and side stop surfaces 32a, 32b of plate 10 when plate 60 is slidingly engaged with plate 10. As with contoured plate 10, these sliding elements 86, 88, 90a, 90b, 92a, and 92b of plate 60, either in combination or alone, may assist in controlling the transverse sliding movement of securing plate 60 as it engages plate 10. Protrusions 90a, 90b may be especially useful in maintaining the proper alignment of plate 60 as it engages plate 10. Accordingly, side ledges 30a, 30b and/or side stop surfaces 32a, 32b of plate 10 may also serve an important role in maintaining the proper alignment of plates 10 and 60.

Securing plate 60 may similarly have structures that may assist in limiting the longitudinal translation of plate 60 within the recess 24 of contoured plate 10. End stop surfaces 94a, 94b may abut end stop surfaces 36a, 36b when securing plate 60 has reached a maximum translation within the recess 24 of contoured plate 10. Similarly, curved surfaces 96a, 96b and end edges 98a, 98b may engage engaging stop surface 38, curved stop surface 40, and/or angled end surface 58 when securing plate 60 has reached a maximum translation within the recess 24 of contoured plate 10. Stop surfaces 94a, 94b, 96a, 96b, 98a, and 98b may therefore, alone or in combination, assist in preventing securing plate 60 from extending too far into contoured plate 10, and may therefore set a minimum length of a fixation assembly comprising plates 10 and 60.

Figure 4A:
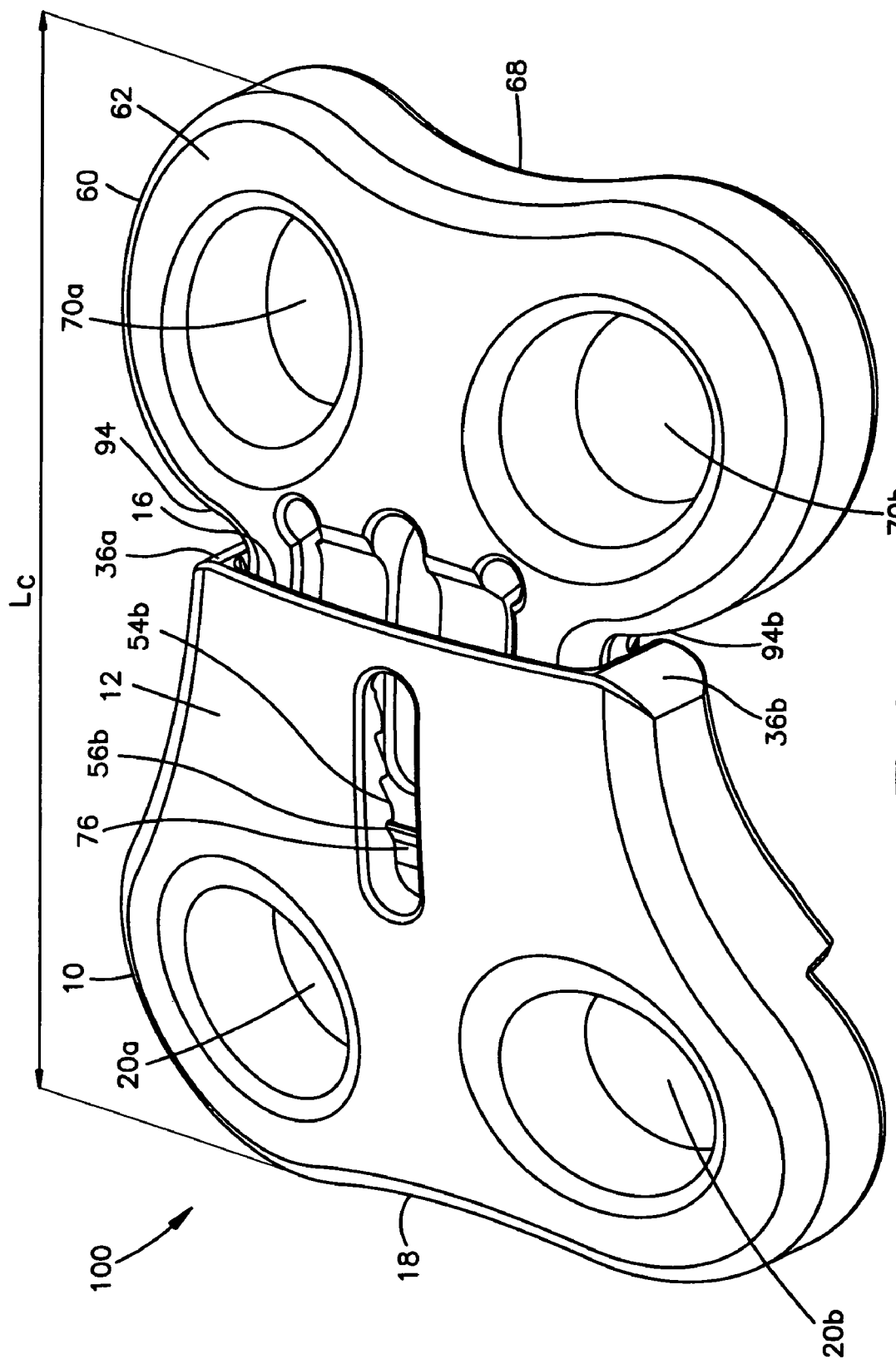
FIG. 4A is a perspective view of the assembly of FIG. 3A in a compressed position.

It is noted that the assemblies 100 of FIGS. 4A-4B, shown in a compressed state, may not result in stop surfaces 36a, 36b of contoured plate 10 abutting stop surfaces 94a, 94b of securing plate 60. It may still be beneficial to have such stop surfaces, however, as plates 10 and 60 may come in different sizes and dimensions so that stop surfaces 36a, 36b do abut stop surfaces 94a, 94b when assembly 100 is in a compressed state.

FIGS. 3A-4B show views of fixation assembly 100 comprising a contoured plate 10 and securing plate 60 and having a longitudinal axis E-E. FIGS. 3A-3B show the assembly 100 in an expanded state, wherein the securing element 74 of plate 60 is engaging the first set of teeth 50a, 50b. In an expanded state, assembly 100 may have a length $L_E$, which may be from about 10 mm to about 200 mm. FIGS. 4A-4B show the assembly 100 in a compressed state, wherein the securing element 74 of plate 60 engages third set of teeth 54a, 54b. In a compressed state, assembly 100 may have a length $L_C$, which may be from about 5 mm to about 200 mm.

Figure 3C:
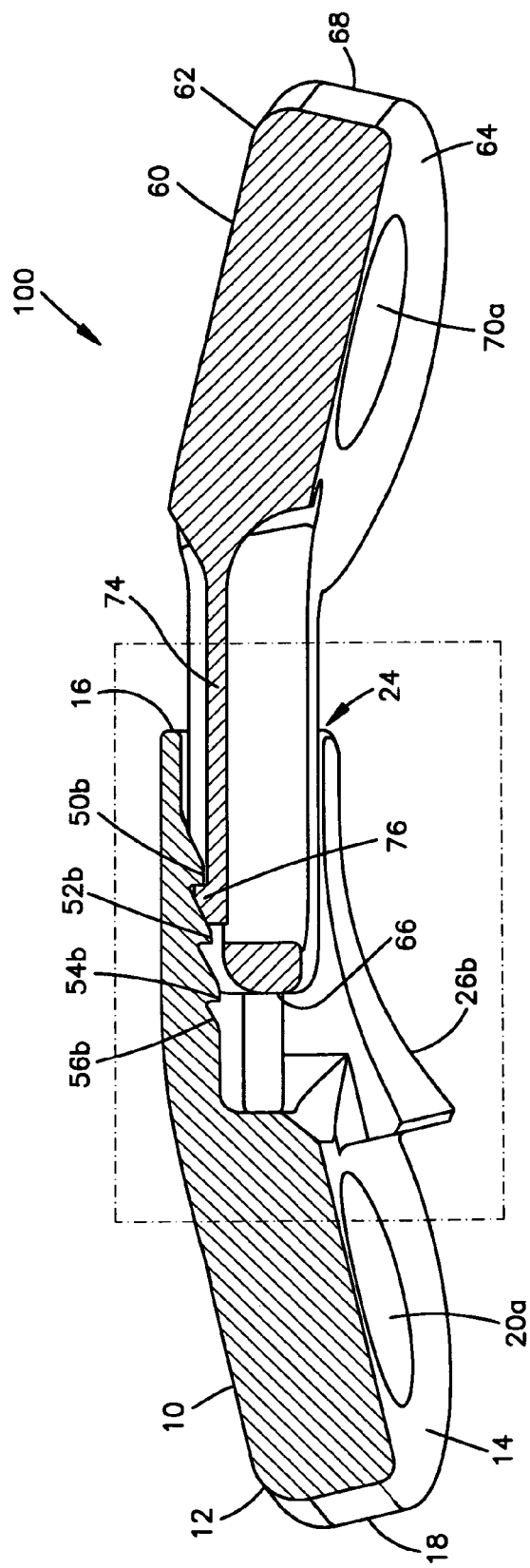
FIG. 3C is a cross-sectional view of the assembly of FIG. 3B taken along the line H-H.
Figure 3D:
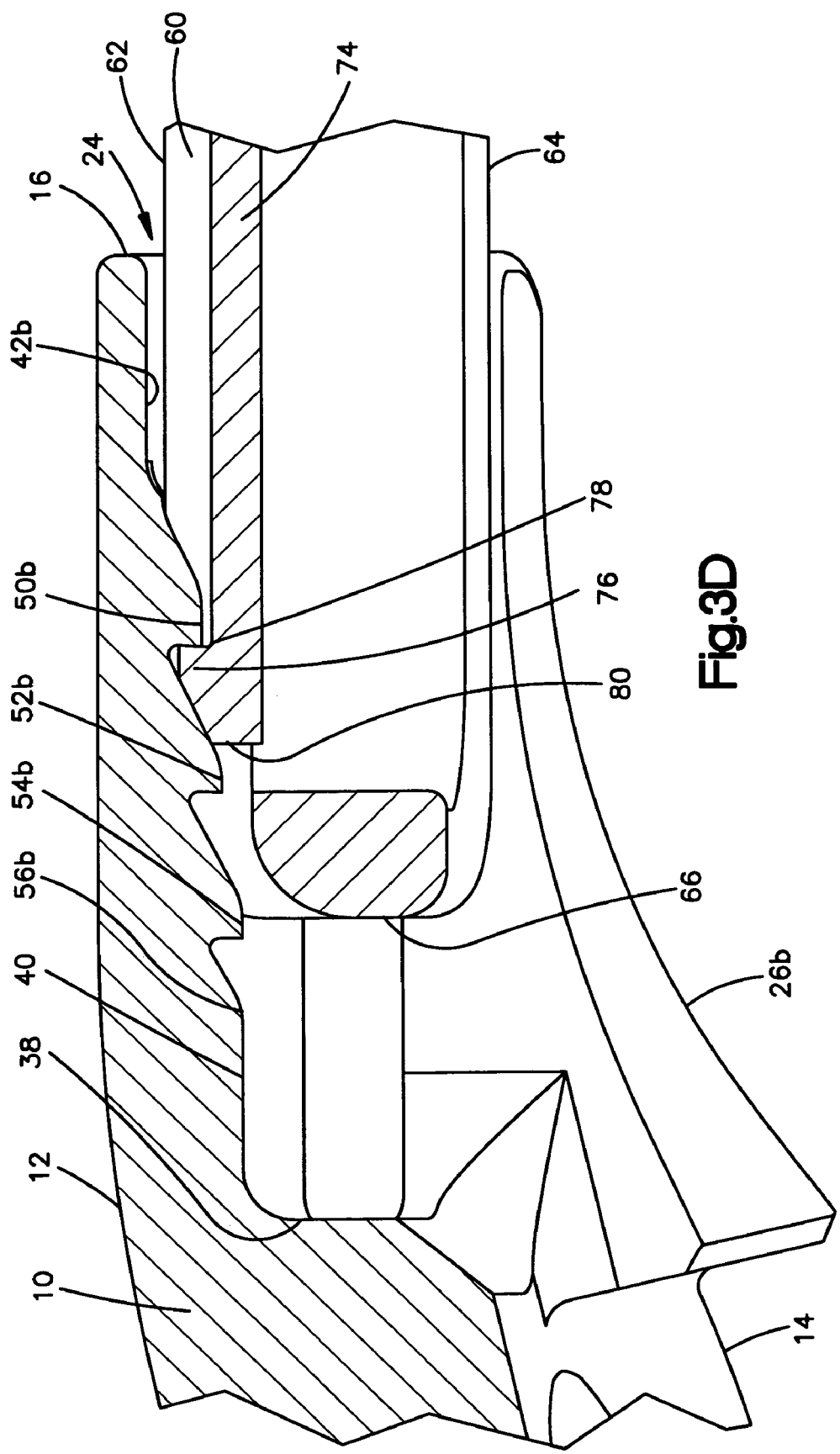
FIG. 3D is an enlarged partial cross-sectional view of the assembly of FIG. 3B.

FIGS. 3C-3D more particularly show the engagement between plates 10 and 60. FIG. 3C is a cross-sectional view of the assembly 100 of FIG. 3B. The engagement of tab 74 with first tooth 50b is evident by FIG. 3C. FIG. 3C also shows a portion of securing plate 60 received within recess 24 of contoured plate 10. FIG. 3D is an enlarged partial cross-sectional view of the assembly 100 of FIG. 3B, showing the engagement of plates 10 and 60 in greater detail.

In use with a intervertebral spacer inserted between two adjacent vertebrae, a surgeon should attach assembly 100 to adjacent vertebrae when the assembly is in an expanded state. The surgeon may choose to manually compress the assembly 100 intraoperatively, as discussed above. Post-operatively, as the vertebrae move toward each other, and as the spacer resorps into the endplates of the vertebrae (if the spacer is made from a resorbable material, such as bone), there may be forces exerted on the assembly 100 urging plates 10 and 60 toward one another. In the embodiment shown in FIGS. 3A-4B, it is the variable engagement of the securing element 74 and teeth 50a, 50b, 52a, 52b, 54a, 54b and ramped surfaces 56a, 56b that may allow for the compression of assembly 100 post-operatively as these forces occur. However, as shown in the embodiment of FIG. 1C, the progressively higher base elevations $B_1$, $B_2$, $B_3$ and peak elevations $P_1$, $P_2$, $P_3$ may require increased compressive force to compress plates 10 and 60 such that securing element 74 may reach the next teeth or ramped surface. This arrangement may be beneficial to ensure that a sufficiently large, and preferably maximum, compressive force is maintained on the graft spacer, while concurrently protecting the fastener to bone interface.

It should also be noted that, in the embodiment shown in FIGS. 1A-4B, the engagement relationship between the enlarged tab 76 and engaging ridge 78 of the securing element 74 and the teeth 50a, 50b, 52a, 52b, 54a, 54b and ramped surfaces 56a, 56b is such that relative extension and disengagement of contoured plate 10 and securing plate 60 is prevented. This feature may be beneficial to prevent post-operative expansion and/or separation of assembly 100, which may be undesirable in light of the risks of spacer expulsion from the disc space and/or vertebral release. More importantly, this feature may also be advantageous to maintain compression on the affected intervertebral space and accompanying graft spacer, to promote fusion.

Figure 5A:
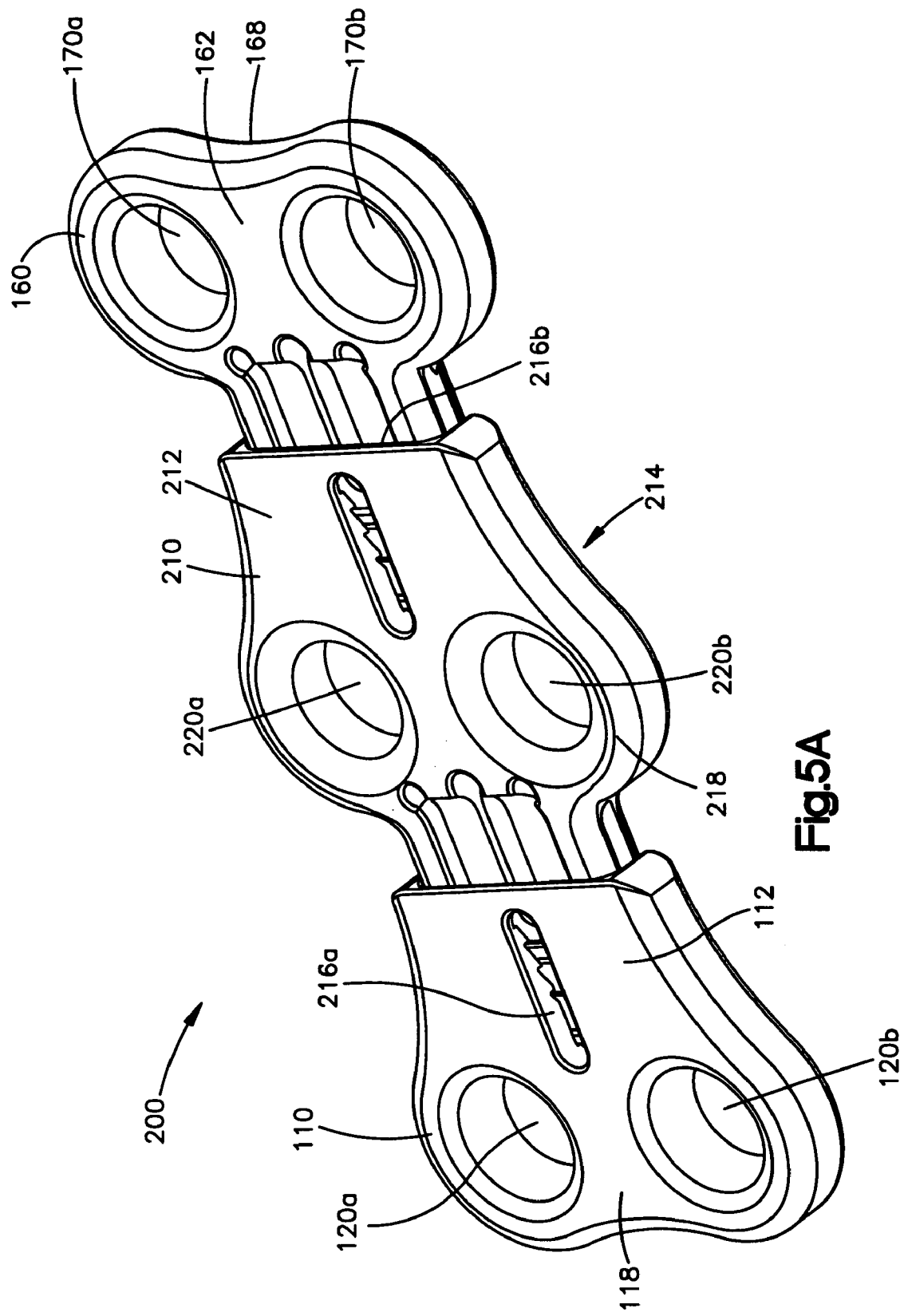
FIG. 5A is a perspective view of an embodiment of a two-level fixation assembly including an intermediate plate.
Figure 5B:
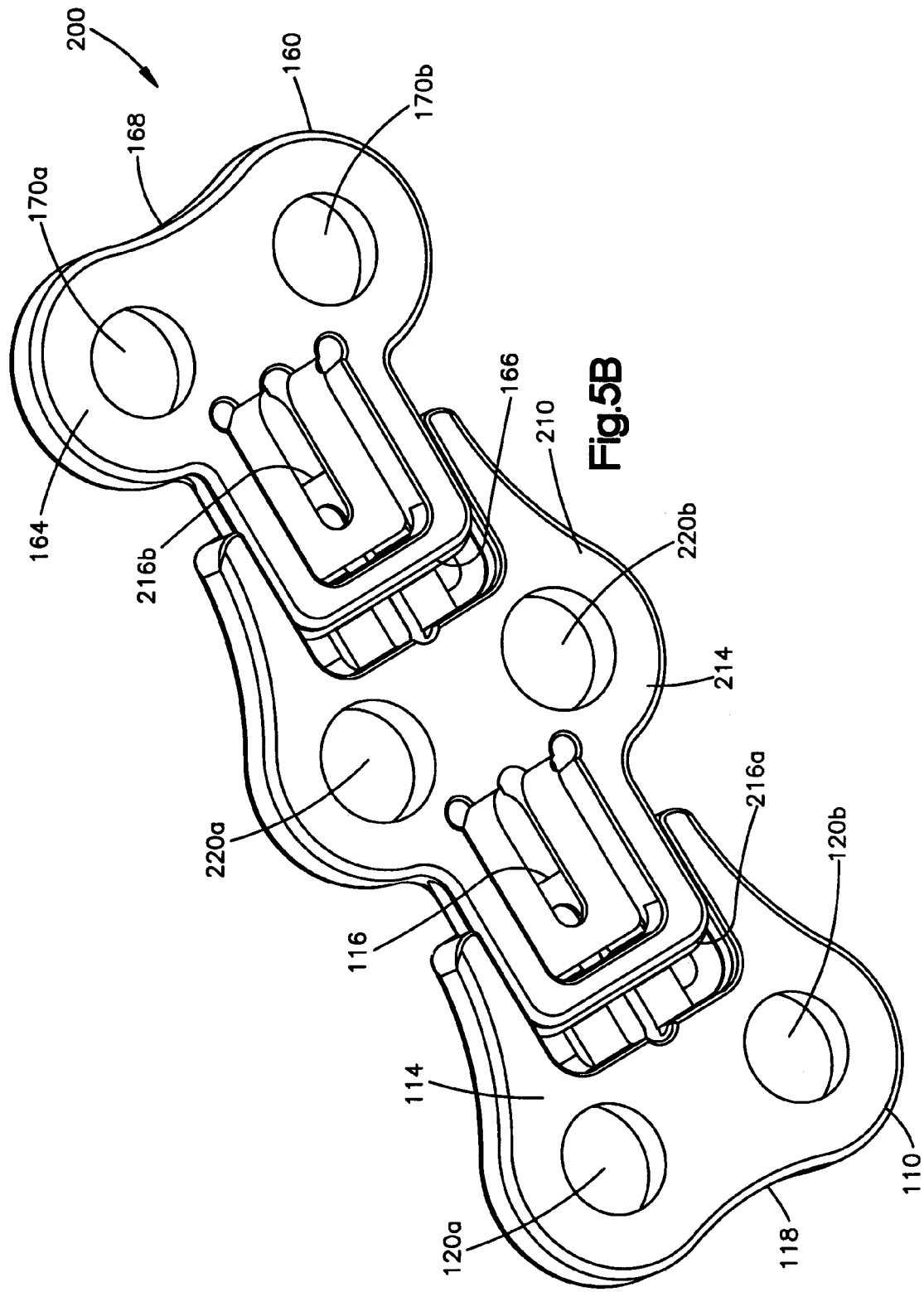
FIG. 5B is another perspective view of the assembly of FIG. 5B.

FIGS. 5A-5B show another embodiment of a fixation assembly utilizing the variable compressive features of plates 10 and 60 described above. Assembly 200 is a two-level assembly, that may comprise a contoured plate 110, a securing plate 160, and an intermediate plate 210. Contoured plate 110 may have an upper surface 112, lower surface 114, engaging end 116, fastening end 118, and fastener holes 120a, 120b. Likewise, securing plate 160 may have an upper surface 162, lower surface 164, engaging end 166, fastening end 168, and fastener holes 170a, 170b. As shown in the embodiment shown in FIGS. 5A-5B, intermediate plate 210 may be positioned between plates 110 and 160 so as to engage both plates. Moreover, intermediate plate 210 may have an upper surface 212, a lower surface 214. The embodiment of the intermediate plate 210 shown in FIGS. 5A-5B additionally has two fastener holes 220a, 220b, which may exhibit any or all of the characteristics and/or functions of fastener holes described above.

Intermediate plate 210 may also have a first engaging end 216a, a second engaging end 216b, with a fastening portion 218 disposed therebetween. As shown in FIGS. 5A-5B, first engaging end 216a and surrounding area of intermediate plate 210 may substantially mimic the characteristics and functions of the securing plate 60, 160, discussed above. Similarly, the second engaging end 216b and surrounding area of intermediate plate 210 may substantially mimic the characteristics and functions of the contoured plate 10, 110, also discussed above.

Assembly 200 may be useful in applications where more than two vertebrae require fixation. While assembly 200 is configured to be used in a two-level assembly, fastening three adjacent vertebrae, it is expressly contemplated that assembly 200 may be configured in a three-level, four-level, or other multi-level assembly to sufficiently meet desired fixation objectives. Contoured plate 110 and securing plate 160 may have any or all of the characteristics and functions of corresponding plates 10 and 60, as described in detail above.

FIGS. 6A-6B show another embodiment a fixation assembly utilizing the variable compressive features of plates 10 and 60 described above. Assembly 300 is configured in a corpectomy model, wherein the assembly 300 is designed to span a space including at least one removed vertebrae, and may comprise a contoured plate 310 and a securing plate 360. Contoured plate 310 may have an upper surface 312, lower surface 314, engaging end 316, fastening end 318, and fastener holes 320a, 320b. Contoured plate 310 may also have an elongated body portion 311 extending between engaging end 316 and fastening end 318. Securing plate 360 may likewise have an upper surface 362, lower surface 364, engaging end 366, fastening end 368, and fastener holes 370a, 370b. Securing plate may also have an elongated body portion 361 extending between engaging end 366 and fastening end 368, and may have a securing element 374 which may have any or all of the characteristics of securing element 74 described in relation to securing plate 60, described above. Moreover, contoured plate 310 and securing plate 360 may have any or all of the characteristics and functions of corresponding plates 10 and 60, as described in detail above.

Assembly 300 may be beneficial in corpectomy procedures to provide a more streamlined assembly with a lower profile, as attachment to intermediate vertebrae is unnecessary because the have been at least partially removed. Body portions 311, 361 therefore may serve to effectively span the length between attached vertebrae without unnecessary fastener holes or other features.

Figure 7A:
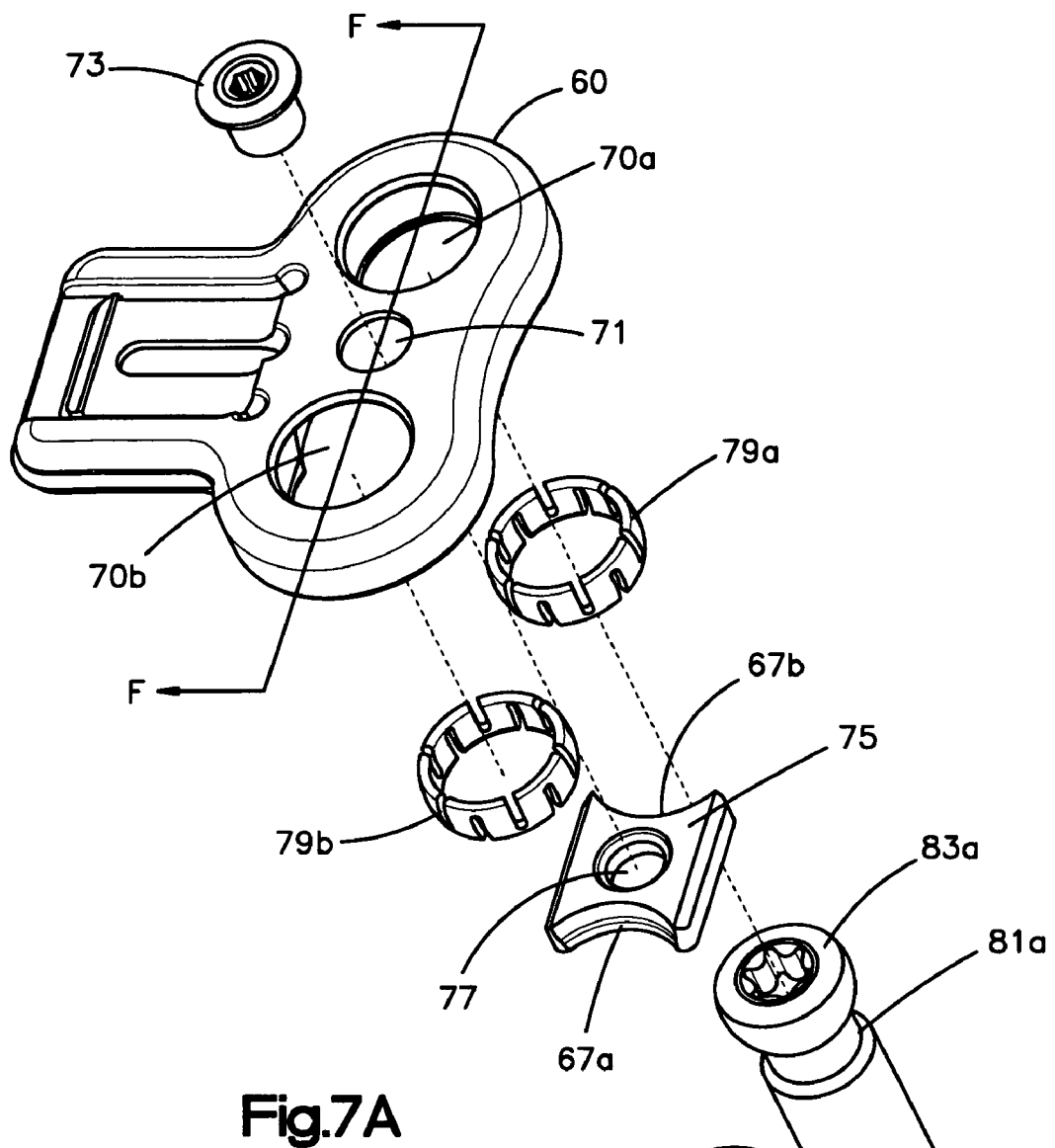
FIG. 7A is an exploded view of an embodiment of a fastener-securing assembly for use with a plate.
Figure 7B:
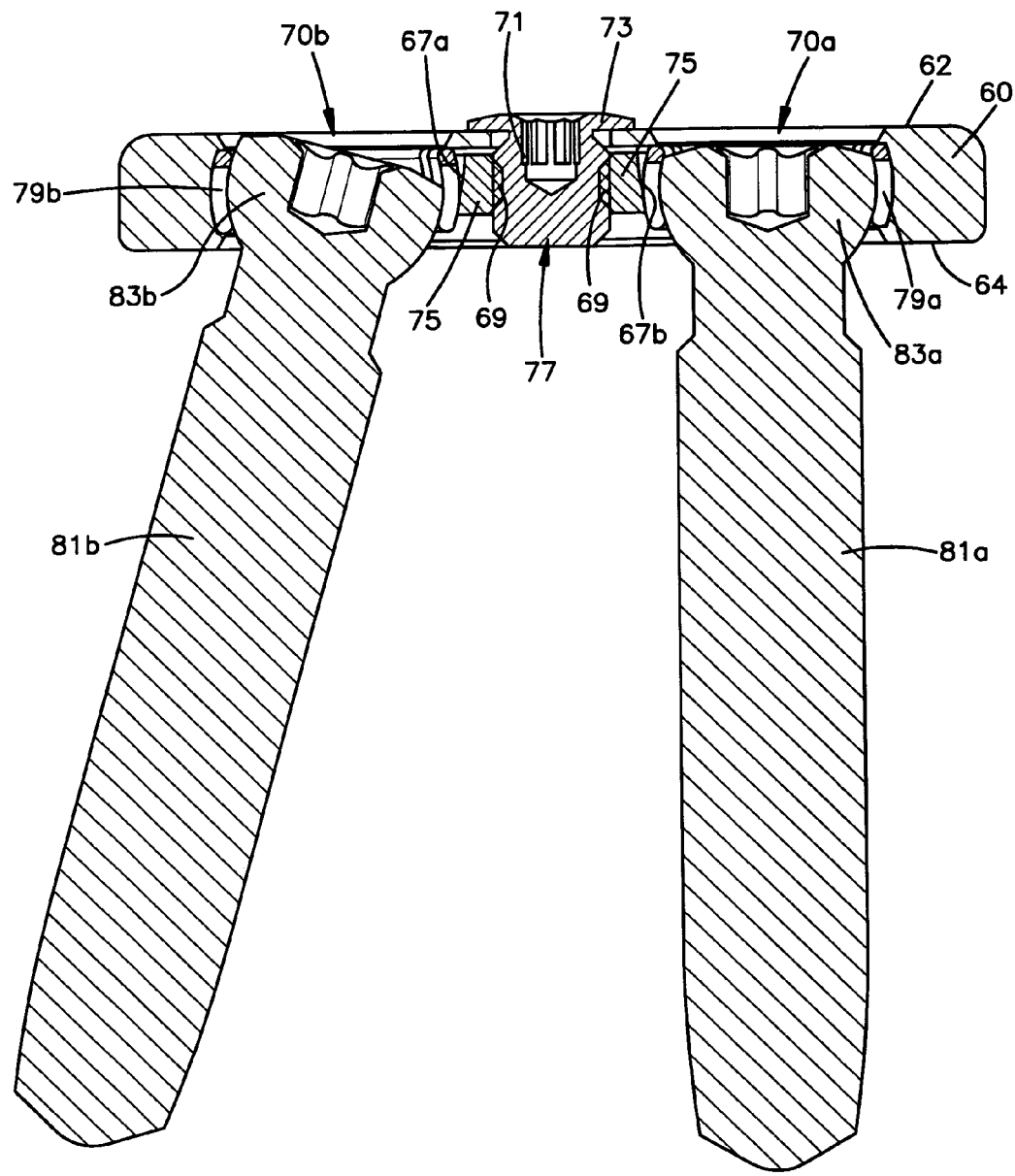
FIG. 7B is a cross-sectional view of the assembly of FIG. 7A in assembled form, taken along the line F-F.

FIGS. 7A-7B show an embodiment of a fastener-securing assembly for use with any or all of the plates 10, 60, 110, 160, 210, 310, 360 described above. FIG. 7A shows an exploded view of the assembly as used with securing plate 60. In this embodiment, securing plate 60 has a fixation hole 71 located between fastener holes 70a, 70b, and extending from the upper surface 62 through the lower surface 64. Fixing element 75 having a threaded bore 77 may be disposed within plate 60, such that fixing element 75 may be disposed between fastener holes 70a, 70b, and threaded bore 77 may substantially align with fixation hole 71. Fixing element 75 may also have ramped surfaces 67a, 67b which may generally slope downwards, as seen in FIG. 7B. Fastener holes 70a, 70b may be fitted with bushings 79a, 79b, that may allow for the polyaxial angulation of fasteners 81a, 81b when the heads 83a, 83b of the fasteners are placed within fastener holes 70a, 70b.

Fasteners 81a, 81b and plates may be "variable angle" or "fixed angle." "Variable angle" refers to fasteners and/or plates for which: (1) the trajectory of insertion of the fastener into bone (through a fastener hole in the plate) may be selected by the surgeon (although only a limited range of motion may be permitted); and/or (2) the trajectory of the fastener with respect to the plate is allowed to change following insertion into bone, for example to toggle to accommodate any translational and/or rotational settling that occur post-operatively between the plate and the fastener that has been rigidly placed into a vertebral body (although only a limited range of motion may be permitted). "Fixed angle" refers to fasteners and/or plates for which: (1) the trajectory of insertion of the fastener into bone (through a fastener hole in the plate) is pre-selected and thus fixed; and/or (2) the trajectory of the fastener with respect to the plate is not allowed to change following insertion into bone. A more detailed discussion of such fastener variations is found in co-pending U.S. patent application Ser. No. 10/653,164, entitled "Bone Plate with Captive Clips," by Duong et al., filed Sep. 3, 2003, the entirety of which is incorporation by reference herein.

In use, fasteners 81a, 81b may be inserted into fastener holes 70a, 70b such that heads 83a, 83b contact bushings 79a, 79b. Once fasteners 81a, 81b have been adjusted to a desired orientation within fastener holes 70a, 70b, a rivet 73 may be inserted into fixation hole 71. Rivet 73 may have threads 69 capable of engaging the threaded bore 77. As rivet 73 is inserted into fixation hole 71, threads 69 may threadedly engage threaded bore 77, urging the fixing element 75 upward toward the upper surface 62 of plate 60. As fixing element 75 is urged upwards, ramped surfaces 67a, 67b may engage the outer surface of bushings 79a, 79b, thereby applying a compressive, radial force on the bushings 79a, 79b, which therefore may secure heads 83a, 83b in the desired orientation within fastener holes 70a, 70b.

It may be beneficial to secure the orientation of fasteners 81a, 81b in a fixed relation to a plate and/or assembly for at least the reason of preventing post-operative fastener backout. Forces within the spinal column may tend to urge inserted fasteners out of vertebral bodies, which may in turn lead to unwarranted and undesirable instability of a plate and/or assembly after implantation. The fastener-securing assembly described above may assist in preventing fastener back-out.

Figure 8B:
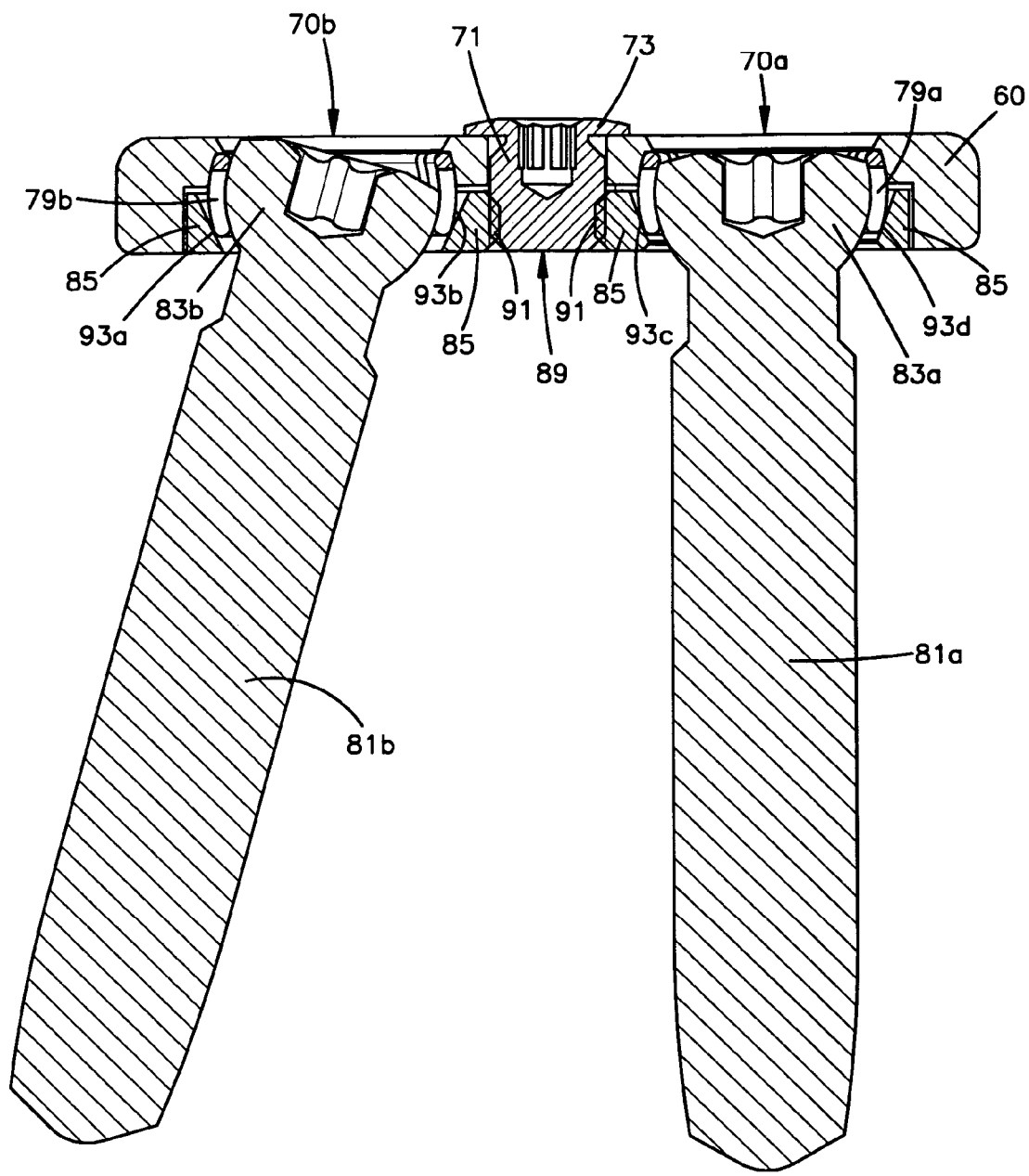
FIG. 8B is a cross-sectional view of the assembly of FIG. 8A in assembled form, taken along the line G-G.

Another embodiment of a fastener-securing assembly is shown in FIGS. 8A-8B. This embodiment is substantially similar in structure to the embodiment shown in FIGS. 7A-7B, but includes a different fixing element 85 with correspondingly different features. As with the previously described design, fixing element 85 may have a threaded bore 89 that, when fixing element is disposed within plate 60, may be substantially aligned with fixation hole 71. However, fixing element 85 in this embodiment has fastener holes 87a, 87b that may substantially align with fastener holes 70a, 70b. Fixing element 85 also may have ramped surfaces 93a, 93b, 93c, 93d that may engage bushings 79a, 79b. In the embodiment shown in FIGS. 8A-8B, fixing element 85 also may be disposed relatively lower within plate 60, as compared to fixing element 75, previously described.

In use, as rivet 73 is inserted into fixation hole 71, and threadedly engages the threaded bore 89 with threads 91, fixing element 85 may be urged upwards into contact with bushings 79a, 79b. Again, ramped surfaces 93a, 93b, 93c, 93d may engage bushings 79a, 79b, such that the fixing element 75 may apply a compressive, radial force on the bushings 79a, 79b, which therefore may secure heads 83a, 83b in the desired orientation within fastener holes 70a, 70b.

It is noted that the above described fastener securing assemblies may be utilized in assemblies wherein fasteners 81a, 81b are inserted into a vertebrae through the fastener holes 70a, 70b of a pre-placed plate 60, or in the alternative, plate 60 may be lowered into engagement with fasteners 81a, 81b after the fasteners have already been inserted into a vertebrae. It may be beneficial to first attach fasteners 81a, 81b, and then apply plate 60 for at least the reason of utilizing the fastener heads 83a, 83b during vertebral distraction techniques prior to graft insertion. Again, these alternatives also apply to each plate 10, 60, 110, 160, 210, 310, 360 described herein.

FIGS. 9A-9D show variations of fastener holes and accompanying bushings for use with any plate described herein. In the embodiments shown in FIGS. 9A-9D, the fastener holes 70a and accompanying upper surface 62 are described in relation to securing plate 60, by way of example. While several of the fastener holes 70a et al. are shown to be substantially circular, it may be preferable to have such fastener holes be a polygonal shape, such as hexagonal (see FIG. 9A) or octagonal (see FIG. 9C). Moreover, a fastener hole 70a may also be fitted with a bushing, regardless of the particular shape of the fastener hole. Generally, bushings may be beneficial to allow a fastener 81a, 81b to toggle and/or rotate within a fastener hole so that a fastener may be inserted at a desired angle. Bushing 79b (discussed supra) demonstrates this advantage with respect to inserted fastener 81b.

Figure 9A:
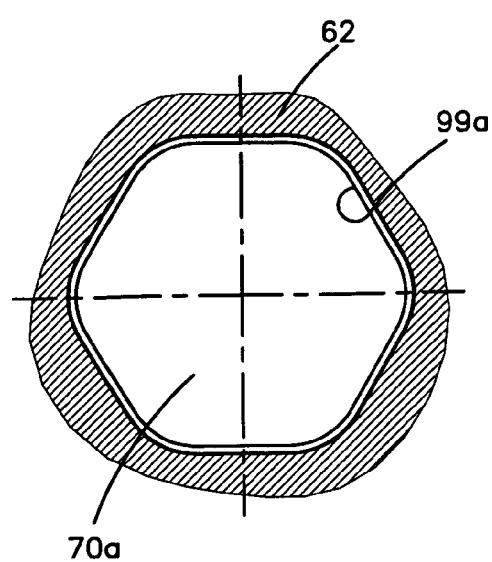
FIG. 9A is a top view of a hexagonal fastener hole for use with a plate.
Figure 9B:
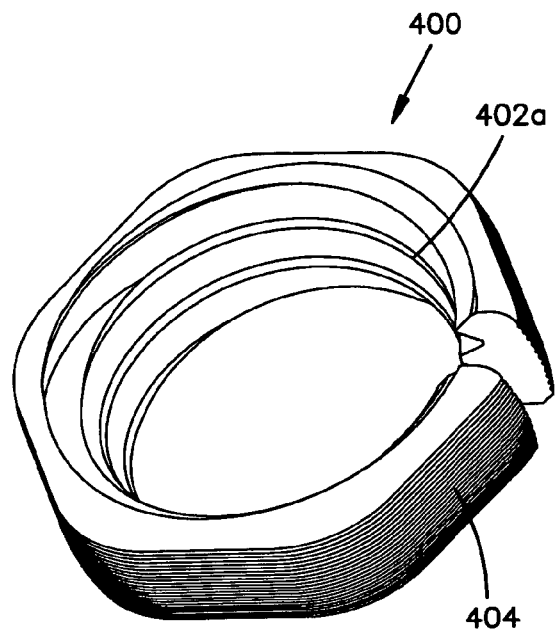
FIG. 9B is a perspective view of a hexagonal bushing for use with the fastener hole of FIG. 9A.
Figure 9C:
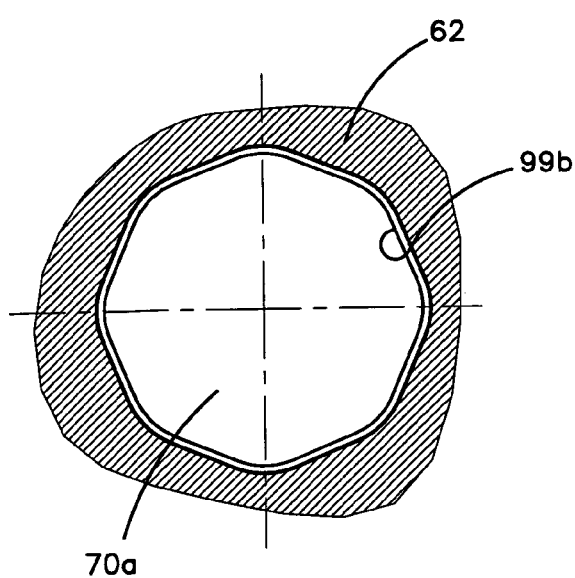
FIG. 9C is a top view of a octagonal fastener hole for use with a plate.
Figure 9D:
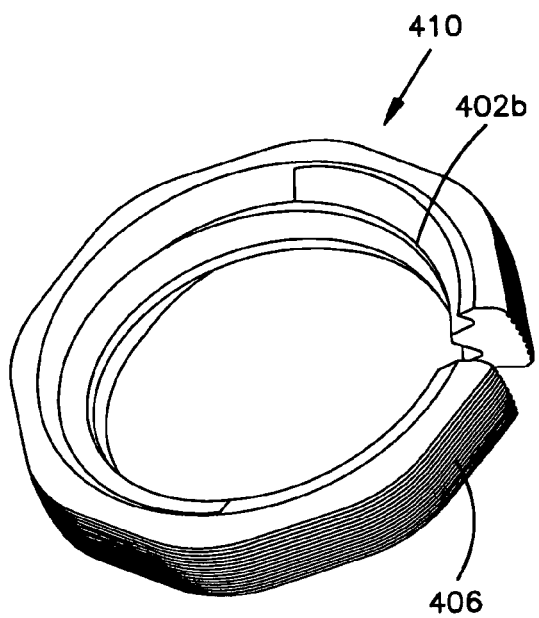
FIG. 9D is a perspective view of an octagonal bushing for use with the fastener hole of FIG. 9C.

FIG. 9B shows a hexagonal bushing 400 with inner threads 402a and an outer surface 404 that may be fitted within fastener hole 70a of FIG. 9A. In use, the outer surface 404 of bushing 400 may lie substantially adjacent the inner surface 99a of fastener hole 70a. FIG. 9D shows an octagonal bushing 410 with inner threads 402b and an outer surface 406 that may be fitted within fastener hole 70a of FIG. 9C. In use, the outer surface 406 of bushing 410 may also lie substantially adjacent the inner surface 99b of fastener hole 70a. It is expressly contemplated that additional shapes of fastener holes and bushings may be used with any or all of the plates described herein, as will be appreciated by those skilled in the art. Further details and advantages of such hole and bushing arrangements is discussed in International Patent Application No. PCT/CH01/00740, entitled "Device for Osteosynthesis", by Synthes AG Chur, the entirety of which is incorporated by reference herein.

It should also be noted that the aforementioned descriptions and illustrations have been provided as examples of the configurations of translation plates that may be designed and assembled using the principles of the invention. These examples will be understood to one of ordinary skill in the art as being non-limiting in that a translating plate employing one or more of the disclosed features may be produced as desired or required for a particular patient's need. Thus, the features disclosed are "modular" in nature.

Each of the fasteners, plates, and other components disclosed herein may be formed of a titanium alloy such as titanium-aluminum-niobium, which may be anodized. One material for use with each of the plates and screws described herein is Ti-6Al-7Nb, with a density of about 4.52 gm/cc, a modulus of elasticity of about 105 GPa, an ultimate tensile strength of about 900 MPa, and a yield strength of about 800 MPa. Surfaces of the fasteners may also be burr free, with all sharp edges having a radius to a maximum of about 0.1 mm. It is expressly contemplated that each of the fasteners, plates, and other components may be comprised of other suitable materials, in addition to the one mentioned herein, as desired by those skilled in the art.

While the invention has been shown and described herein with reference to particular embodiments, it is to be understood that the various additions, substitutions, or modifications of form, structure, arrangement, proportions, materials, and components and otherwise, used in the practice and which are particularly adapted to specific environments and operative requirements, may be made to the described embodiments without departing from the spirit and scope of the present invention. Accordingly, it should be understood that the embodiments disclosed herein are merely illustrative of the principles of the invention. Various other modifications may be made by those skilled in the art which will embody the principles of the invention and fall within the spirit and the scope thereof.

What is claimed:

1. A fixation assembly having a longitudinal axis comprising:
    a first plate having an upper surface and a lower surface, at least one first fastener hole configured to receive a first fastener, the first fastener hole extending from the upper surface through to the lower surface, a plurality of rows of teeth and at least one ramped surface on the lower surface of the first plate, wherein a first row of teeth of the plurality of rows of teeth has a first elevation, and a second row of the plurality of rows of teeth has a second elevation and the second elevation is greater than the first elevation; and
    a second plate having an upper surface and a lower surface, at least one second fastener hole configured to receive a second fastener, and a deflectable resilient securing element on the upper surface, the resilient securing element comprising an enlarged tab and an engaging ridge, the tab and the engaging rib engageable with the at least one of the plurality of rows of teeth to couple the plates together;
    wherein the second plate is movable along the longitudinal axis with respect to the first plate; and wherein the compressive force necessary to engage the resilient element with subsequent rows of teeth of the plurality of rows of teeth increases as the second plate moves farther along the longitudinal axis.

2. The assembly of claim 1, further comprising a third plate mounted to at least one of the first and second plates.

3. The assembly of claim 1, wherein the plurality of rows of teeth comprises at least three rows of teeth.

4. The assembly of claim 1, wherein at least one of the first and second fasteners is a bone screw.

5. The assembly of claim 4, wherein the bone screw is a self-drilling bone screw.

6. The assembly of claim 4, wherein the bone screw is a self-tapping bone screw.

7. The assembly of claim 4, wherein the bone screw toggles within at least one of the first and second fastener hole.

8. The assembly of claim 1, wherein the first and second plate each further include a window.

* * * * *